(12) United States Patent
Pschirer et al.

(10) Patent No.: US 8,569,500 B2
(45) Date of Patent: Oct. 29, 2013

(54) TERRYLENE AND QUATERRYLENE DERIVATIVES

(75) Inventors: Neil Gregory Pschirer, Mainz (DE); Jianqiang Qu, Ludwigshafen (DE); Martin Koenemann, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 350 days.

(21) Appl. No.: 12/849,079

(22) Filed: Aug. 3, 2010

(65) Prior Publication Data

US 2010/0317876 A1 Dec. 16, 2010

Related U.S. Application Data

(62) Division of application No. 11/913,333, filed as application No. PCT/EP2006/062015 on May 3, 2006, now Pat. No. 7,795,431.

(30) Foreign Application Priority Data

May 4, 2005 (DE) .......................... 10 2005 021 362

(51) Int. Cl.
   *C07D 471/00* (2006.01)
   *C07D 491/00* (2006.01)
   *C07D 498/00* (2006.01)

(52) U.S. Cl.
   USPC ........................................................ 546/27

(58) Field of Classification Search
   USPC ........................................................ 546/27
   See application file for complete search history.

(56) References Cited

U.S. PATENT DOCUMENTS

| 5,405,962 | A | 4/1995 | Muellen et al. |
| 5,508,137 | A | 4/1996 | Langhals |
| 5,986,099 | A | 11/1999 | Muellen et al. |
| 6,124,458 | A | 9/2000 | Muellen et al. |
| 6,878,825 | B2 | 4/2005 | Krieger et al. |
| 7,138,522 | B2 | 11/2006 | Krieger et al. |
| 7,145,010 | B2 | 12/2006 | Boehm et al. |
| 2005/0222416 | A1 | 10/2005 | Bohm et al. |
| 2008/0167467 | A1 | 7/2008 | Konemann et al. |
| 2008/0269482 | A1 | 10/2008 | Pschirer et al. |

FOREIGN PATENT DOCUMENTS

| EP | 0 596 292 A1 | 5/1994 |
| EP | 0 638 613 A1 | 2/1995 |
| WO | WO 96/22332 | 7/1996 |
| WO | WO 02/066438 A1 | 8/2002 |
| WO | WO 02/076988 A2 | 10/2002 |
| WO | WO 03/104232 A1 | 12/2003 |

OTHER PUBLICATIONS

Li, et al., Synthesis and characterization of 3,5-bis(2-hydroxyphenyl)-1,2,4-triazole functionalized tetraaryloxy perylene bisimide and metal-directed self-assembly, Journal of Organic Chemistry, 70(24), 9686-9692 (2005).*
Li, et al Synthesis and Characterization of 3,5-bis(2-hydroxyphenyl)-1,2,4-triazole Functionalized Tetraaryloxy Perylene Bisimide and Metal-directed Self-assembly, Journal of Organic Chemistry, 70(24), 9686-9692 (2005).*
Carsten Former, et al., "Cyclodehydrogenation of Poly (perylene) to Poly (quarterryllene): Toward Poly (*peri*naphthalene)"American Chemical Society, XP-002219190, pp. 1576-1582.
Yves Geerts, et al., "Quaterrylenebis (dicarboximide)s: near infrared absorbing and emitting dyes", Journal of Material s Chemistry, XP-000803180, pp. 2357-2369.
Frank O. Holtrup, et al., "Terrylenimides: New NIR Fluorescent Dyes", Chemistry—A European Journal, XP-000931226, pp. 219-225.
Fabian Nolde, et al., "Synthesis and Modification of Terrylenediimides as High Performance Fluorescent Dyes", Chemistry—A European Journal, XP-002365259, pp. 3959-3967.
Former, et al., "Cyclodehydrogenation of poly(perylene) to poly(quaterrylane): toward poly(pery-naphthalene)", Macromolecules, vol. 35, No. 5, 1576-82, 2002.
Nolde, et al., "Synthesis and Modification of Terrylenediimines as High-Performance Fluorescent Dyes," Chem. Eur. J., 11, 3959-3967, 2005.

* cited by examiner

*Primary Examiner* — Erich A Leeser
(74) *Attorney, Agent, or Firm* — Oblon, Spivak, McClelland, Maier & Neustadt, L.L.P.

(57) ABSTRACT

A process for preparing a rylenetetracarboxylic dianhydride, or a salt thereof having application formula Ib by subjecting a rylenetetracarboximide of application formula II to a hydrolysis under alkaline conditions in the presence of a polar organic solvent and removing the rylenetetracarboxylic dianhydride Ib from any rylenetetracarboxylic monoimide monoanhydride of application formula Ia which is formed to form the rylenetetracarboxylic dianhydride, or the salt thereof having formula Ib; or hydrolyzing the rylenetetracarboximide of application formula II under conditions that form the compound of application formula Ib and substantially no rylenetetracarboxylic monoimide monoanhydride of application formula Ia.

12 Claims, No Drawings

TERRYLENE AND QUATERRYLENE DERIVATIVES

CROSS REFERENCE TO RELATED APPLICATIONS

This application is a divisional of U.S. patent application Ser. No. 11/913,333, filed Nov. 1, 2007 which is the U.S. national stage of International Application No. PCT/EP06/62015, filed May 3, 2006, the disclosures of which are incorporated herein by reference in their entireties. This application claims priority to German Patent Application 10 2005 021 362.6, filed May 4, 2005, the disclosures of which are incorporated herein by reference in their entireties.

DESCRIPTION

The present invention relates to novel rylene derivatives of the general formula I

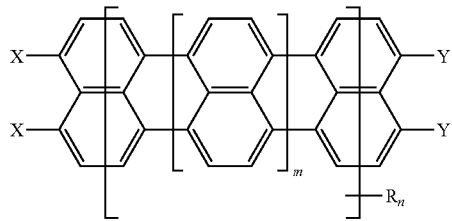

in which the variables are each defined as follows:
X are joined to one another with formation of a six-membered ring to give a radical of the formula (a), (b) or (c)

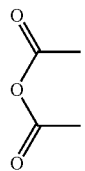

(a)

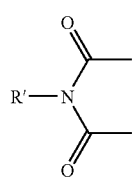

(b)

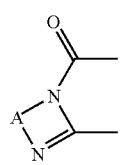

(c)

are both a —COOM radical;
are both hydrogen or one of the two radicals is hydrogen and the other radical is halogen or a radical of the formula (d)

(d)

Y are joined to one another with formation of a six-membered ring to give a radical of the formula (a) when one of the two X radicals is hydrogen and the other X radical is halogen or a radical of the formula (d) or when both X radicals are hydrogen or together are a radical of the formula (a), (b) or (c);
are joined to one another with formation of a six-membered ring to give a radical of the formula (b) when one of the two X radicals is hydrogen and the other X radical is halogen or a radical of the formula (d) or when both X radicals are hydrogen or a —COOM radical or together are a radical of the formula (c);
are joined to one another with formation of a six-membered ring to give a radical of the formula (c) when one of the two X radicals is hydrogen and the other X radical is halogen or a radical of the formula (d) or when both X radicals are hydrogen or a —COOM radical or together are a radical of the formula (c) which may be arranged in the cis or trans position to the other (c) radical;
are both a —COOM radical when one of the two X radicals is hydrogen and the other X radical is halogen or a radical of the formula (d) or when both X radicals are hydrogen or a —COOM radical, M being different from hydrogen in the case that one X radical is a radical of the formula (d);
are both hydrogen or one of the two radicals is hydrogen and the other radical is halogen or a radical of the formula (d) when both X radicals are hydrogen or one of the two X radicals is hydrogen and the other X radical is halogen or a radical of the formula (d);
R are identical or different radicals:
aryloxy, arylthio, hetaryloxy or hetarylthio, to each of which may be fused further saturated or unsaturated 5- to 7-membered rings whose carbon skeleton may be interrupted by one or more —O—, —S—, —NR$^1$—, —N=CR$^1$—, —CO—, —SO— and/or —SO$_2$— moieties, where the entire ring system may be mono- or polysubstituted by the (i), (ii), (iii), (iv) and/or (v) radicals:
(i) C$_1$-C$_{30}$-alkyl whose carbon chain may be interrupted by one or more —O—, —S—, —NR$^1$—, —N=CR$^1$—, —C≡C—, —CR$^1$=CR$^1$—, —CO—, —SO— and/or —SO$_2$— moieties and which may be mono- or polysubstituted by: C$_1$-C$_{12}$-alkoxy, C$_1$-C$_6$-alkylthio, —C≡CR$^1$, —CR$^1$=CR$^1$$_2$, hydroxyl, mercapto, halogen, cyano, nitro, —NR$^2$R$^3$, —NR$^2$COR$^3$, —CONR$^2$R$^3$, —SO$_2$NR$^2$R$^3$, —COOR$^2$, —SO$_3$R$^2$, —PR$^2$R$^3$, —POR$^2$R$^3$, aryl and/or saturated or unsaturated C$_4$-C$_7$-cycloalkyl whose carbon skeleton may be interrupted by one or more —O—, —S—, —NR$^1$—, —N=CR$^1$—, —CR$^1$=CR$^1$—, —CO—, —SO— and/or —SO$_2$— moieties, where the aryl and cycloalkyl radicals may each be mono- or polysubstituted by C$_1$-C$_{18}$-alkyl and/or the above radicals specified as substituents for alkyl;

(ii) $C_3$-$C_8$-cycloalkyl whose carbon skeleton may be interrupted by one or more —O—, —S—, —$NR^1$—, —N=$CR^1$—, —$CR^1$=$CR^1$—, —CO—, —SO— and/or —$SO_2$— moieties and to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iii) aryl or hetaryl to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by: $C_1$-$C_{18}$-alkyl, $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$, —$POR^2R^3$, aryl and/or hetaryl, each of which may be mono- or polysubstituted by $C_1$-$C_{18}$-alkyl, $C_1$-$C_{12}$-alkoxy, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

(iv) a —U-aryl radical which may be mono- or polysubstituted by the above radicals specified as substituents for the aryl radicals (iii), where U is a —O—, —S—, —$NR^1$—, —CO—, —SO— or —$SO_2$— moiety;

(v) $C_1$-$C_{12}$-alkoxy, $C_1$-$C_6$-alkylthio, —C≡$CR^1$, —$CR^1$=$CR^1_2$, hydroxyl, mercapto, halogen, cyano, nitro, —$NR^2R^3$, —$NR^2COR^3$, —$CONR^2R^3$, —$SO_2NR^2R^3$, —$COOR^2$, —$SO_3R^2$, —$PR^2R^3$ and/or —$POR^2R^3$;

R' is hydrogen;

$C_1$-$C_{30}$-alkyl whose carbon chain may be interrupted by one or more —O—, —S—, —$NR^1$—, —N=$CR^1$—, —C≡C—, —$CR^1$=$CR^1$—, —CO—, —SO— and/or —$SO_2$— moieties and which may be mono- or polysubstituted by the (ii), (iii), (iv) and/or (v) radicals specified as substituents for the R radicals;

$C_3$-$C_8$-cycloalkyl to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be substituted by the (i), (ii), (iii), (iv) and/or (v) radicals specified as substituents for the R radicals;

aryl or hetaryl to which may be fused further saturated or unsaturated 5- to 7-membered rings whose carbon skeleton may be interrupted by one or more —O—, —S—, —$NR^1$—, —N=$CR^1$—, —$CR^1$=$CR^1$—, —CO—, —SO— and/or —$SO_2$— moieties, where the entire ring system may be mono- or polysubstituted by the (i), (ii), (iii), (iv), (v) radicals specified as substituents for the R radicals, and/or aryl- and/or hetarylazo, each of which may be mono- or polysubstituted by $C_1$-$C_{10}$-alkyl, $C_1$-$C_6$-alkoxy and/or cyano;

A is in each case independently phenylene, naphthylene or pyridylene, each of which may be mono- or polysubstituted by $C_1$-$C_{12}$-alkyl, $C_1$-$C_6$-alkoxy, hydroxyl, nitro and/or halogen;

M is hydrogen, ammonium or alkali metal cation;

R" is in each case independently hydrogen, $C_1$-$C_{30}$-alkyl, $C_5$-$C_8$-cycloalkyl, aryl or hetaryl or, joined together with formation of a 5-membered ring which comprises the two oxygen atoms and also the boron atom, which may be substituted on the carbon atoms by up to 4 $C_1$-$C_{30}$-alkyl, $C_5$-$C_8$-cycloalkyl, aryl and/or hetaryl groups;

$R^1$ is hydrogen or $C_1$-$C_{18}$-alkyl, where the $R^1$ radicals may be the same or different when they occur more than once;

$R^2$, $R^3$ are each independently hydrogen;

$C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^1$;

aryl or hetaryl to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl;

m is 1 or 2;

n is from 3 to 6 where m=1;

is from 2 to 8 where m=2, and mixtures thereof.

The invention further relates to the preparation of the rylene derivatives I and to their use for coloring high molecular weight organic and inorganic materials, for producing aqueous polymer dispersions which absorb in the near infrared region of the electromagnetic spectrum, for obtaining markings and inscriptions which absorb infrared light and are invisible to the human eye, as infrared absorbers for heat management, as IR laser beam-absorbing materials in the fusion treatment of plastics parts, as semiconductors in organic electronics, as emitters in electro- and chemiluminescence applications, and also as active components in photovoltaics.

Compounds which absorb in the near infrared region of the electromagnetic spectrum are of increasing interest for a multitude of applications. One class of such organic compounds is that of polycyclic conjugated aromatic ring systems based on rylene.

Molecules known to date on the basis of the higher rylenes of particular interest are unsubstituted and tetra- and hexa-halo-substituted and tetra- and hexa-aroxy-substituted quaterrylenetetracarboximides (EP-A-596 292 or WO-A-96/22332 and WO-A-02/76988), unsubstituted and peri-halogenated terrylene and quaterrylenedicarboximides (WO-A-02/66438), and also unsubstituted and tetra-halo- and -aroxy-substituted terrylenetetracarboximides (WO-A-03/104232).

It was an object of the invention to provide further compounds which absorb in the wavelength range from 550 to 900 nm and feature advantageous performance properties, and are in particular functionalized such that they are adapted in a controlled manner to the desired end use or else can be converted to compounds absorbing at even longer wavelengths.

Accordingly, the terrylene and quaterrylene derivatives of the formula I defined at the outset have been found.

Preferred definitions of the variables occurring in formula I can be taken from the subclaims.

The terrylene derivatives I may have from 3 to 6 substituents R; they are preferably tetrasubstituted by substituents in the 1,6,9,14 arrangement.

The quaterrylene derivatives I may bear from 3 to 8 substituents R; they are preferably tetrasubstituted in the 1,6,11,16 arrangement or hexasubstituted in the 1,6,8,11,16,18 or 1,6,8,11,16,19 arrangement.

In general, both the terrylene derivatives and the quaterrylene derivatives I are obtained in the form of mixtures of products with different degrees of substitution, in which the tetrasubstituted product, or else the hexasubstituted product for the quaterrylene derivatives, makes up the majority in each case.

Also found has been a process for preparing rylenetetracarboxylic monoimide monoanhydrides of the general formula Ia

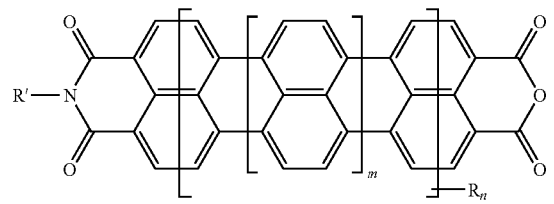

which comprises a) subjecting a rylenetetracarboximide of the general formula II

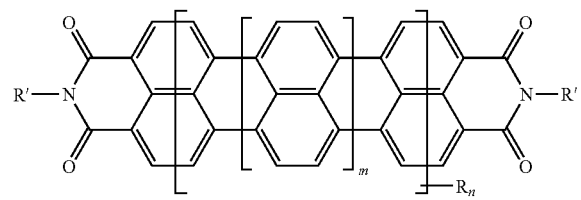

to a hydrolysis under alkaline conditions in the presence of a polar organic solvent and removing the rylenetetracarboxylic monoimide monoanhydride Ia from the rylenetetracarboxylic dianhydride Ib which is likewise formed or b) hydrolyzing the rylenetetracarboximide II by use of mild reaction conditions directly, substantially singly, to the rylenetetracarboxylic monoimide monoanhydride Ia.

Also found has been a process for preparing rylenetetracarboxylic dianhydrides of the general formula Ib

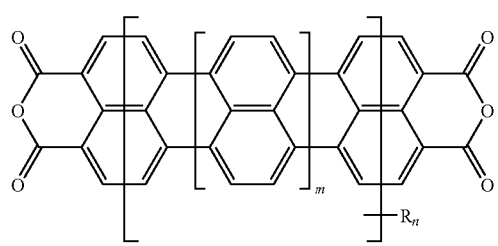

which comprises a) subjecting a rylenetetracarboximide of the general formula II

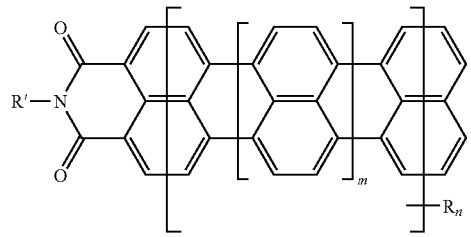

to a hydrolysis under alkaline conditions in the presence of a polar organic solvent and removing the rylenetetracarboxylic dianhydride Ib from the rylenetetracarboxylic monoimide monoanhydride Ia which is likewise formed or b) hydrolyzing the rylenetetracarboximide II by use of more severe reaction conditions directly, substantially on both sides, to the rylenetetracarboxylic dianhydride Ib.

Additionally found has been a process for preparing rylenedicarboximides of the general formula Ic which comprises a) subjecting a rylenetetracarboxylic monoimide monoanhydride of the general formula Ia or
b) subjecting the mixture, obtained in the alkaline hydrolysis of a rylenetetracarboximide of the general formula II

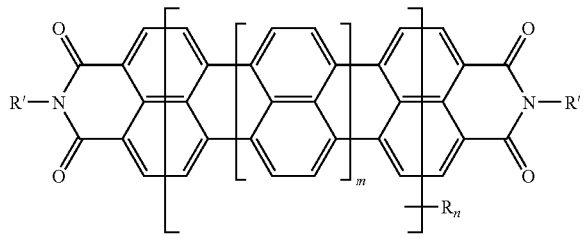

of rylenetetracarboxylic monoimide monoanhydride Ia and rylenetetracarboxylic dianhydride Ib
to a decarboxylation in the presence of a tertiary nitrogen-basic compound as a solvent and of a transition metal catalyst, and, in case b), separating the rylenedicarboximide Ic from the fully decarboxylated rylene Id which likewise forms.

Also found has been a process for preparing rylenes of the general formula Id

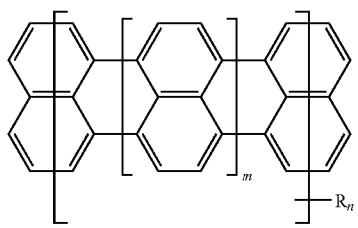

which comprises
a) subjecting a rylenetetracarboxylic dianhydride of the general formula Ib

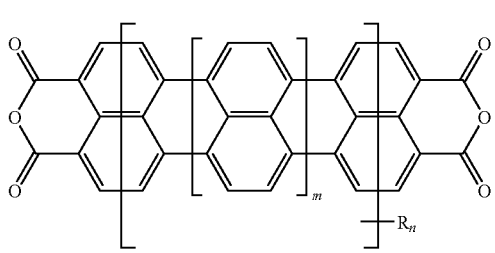

or
b) subjecting the mixture, obtained in the alkaline hydrolysis of a rylenetetracarboximide of the general formula II

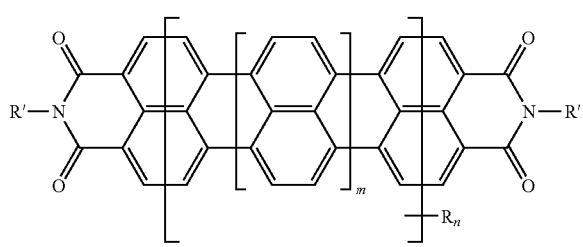

of rylenetetracarboxylic monoimide monoanhydride Ia and rylenetetracarboxylic dianhydride Ib to a decarboxylation in the presence of a tertiary nitrogen-basic compound as a solvent and of a transition metal catalyst, and, in case b), separating the rylene Id from the rylenedicarboximide Ic which likewise forms.

Additionally found has been a process for preparing perihalogenated rylenedicarboximides of the general formula Ie

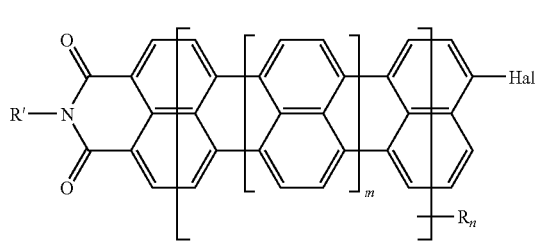

in which Hal is halogen, which comprises
a) reacting a rylenedicarboximide of the general formula Ic

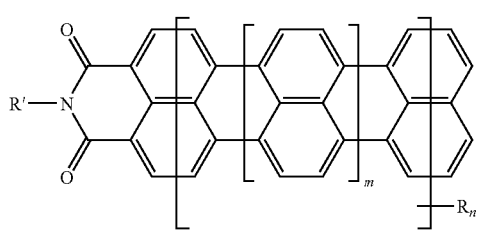

or
b) reacting the mixture of rylenedicarboximide Ic and rylene Id which is obtained in the decarboxylation of the mixture, obtained in the alkaline hydrolysis of the rylenetetracarboximide of the general formula II

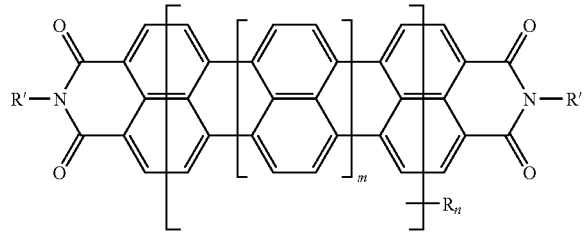

of rylenetetracarboxylic monoimide monoanhydride Ia and rylenetetracarboxylic dianhydride Ib, in the presence of a polar organic solvent and of a Lewis acid as a catalyst, with from 1 to 6 mol of N-halosuccinimide per halogen atom to be introduced, and, in case b), separating the peri-halogenated rylenedicarboximide Ie from the likewise halogenated rylene If.

Also found has been a process for preparing halogenated rylenes of the general formula If

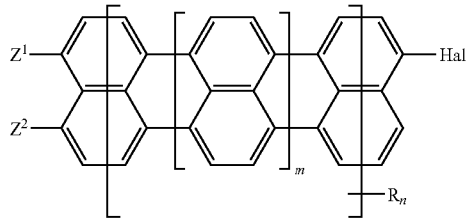

If in which Hal is halogen, $Z^1$ and $Z^2$ are each hydrogen or one of the two $Z^1$ and $Z^2$ radicals is halogen and the other radical is hydrogen, which comprises a) reacting a rylene of the general formula Id

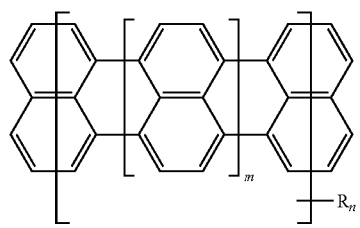

Id in the presence of a polar organic solvent and of a Lewis acid as a catalyst a1) directly with the amount, required to introduce the total number of halogen atoms desired, of from 1 to 6 mol of N-halosuccinimide per halogen atom to be introduced or a2) first with from 1 to 3 mol/mol of N-halosuccinimide to give the monohalogenated rylene If ($Z^1=Z^2=H$) and then with a further from 1 to 6 mol/mol of N-halosuccinimide to give the dihalogenated rylene If ($Z^1$ or $Z^2$=halogen)

or b) reacting the mixture of rylenedicarboximide Ic and rylene Id which is obtained in the decarboxylation of the mixture, obtained in the alkaline hydrolysis of the rylenetetracarboximide of the general formula II

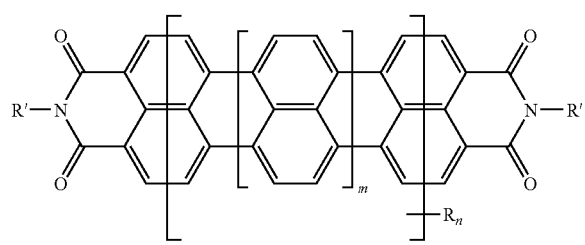

II of rylenetetracarboxylic monoimide monoanhydride Ia and rylenetetracarboxylic dianhydride Ib, in the presence of a polar organic solvent and of a Lewis acid as a catalyst b1) directly with the amount, required to introduce the total number of halogen atoms desired, of from 1 to 6 mol of N-halosuccinimide per halogen atom to be introduced or b2) first with from 1 to 3 mol of N-halosuccinimide per mole of Ic and Id and separating the monohalogenated rylene If ($Z^1=Z^2=H$) from the peri-halogenated rylenedicarboximide Ie which is likewise formed and then reacting with a further from 1 to 6 mol/mol of N-halosuccinimide to give the dihalogenated rylene If ($Z^1$ or $Z^2$=halogen).

Finally found has been a process for preparing rylenedicarboxylic anhydrides Igh

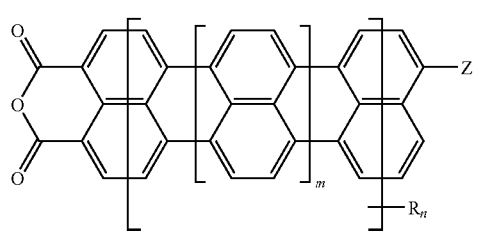

Igh in which Z is hydrogen or halogen, which comprises subjecting a rylenedicarboximide of the general formula Ice

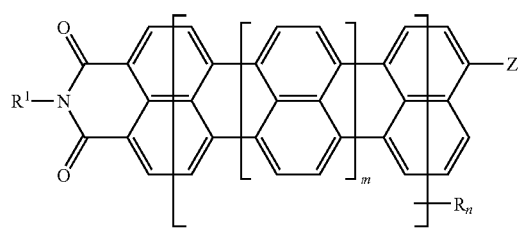

Ice to a hydrolysis under alkaline conditions in the presence of a polar organic solvent.

Also found has been a process for preparing peri-halogenated rylenedicarboxylic anhydrides Ih

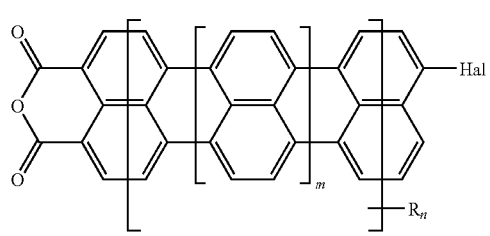

Ih in which Hal is halogen, which comprises reacting a rylenedicarboxylic anhydride of the general formula Ig

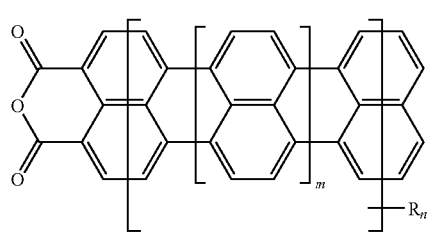

Ig with N-halosuccinimide in the presence of a polar organic solvent and of a Lewis acid.

Additionally found has been a process for preparing peri-(dioxaborolan-2-yl)rylenedicarboximides of the general formula Ii

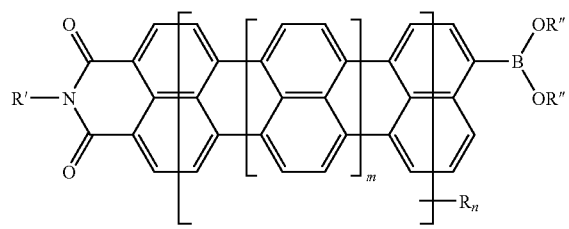

which comprises reacting a peri-halogenated rylenedicarboximide of the general formula Ie

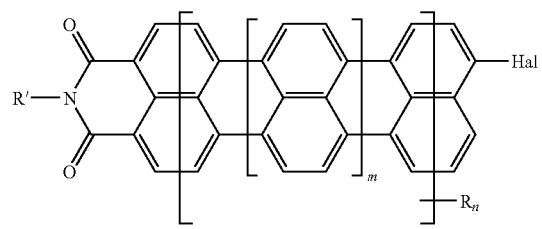

in which Hal is halogen, in the presence of an aprotic organic solvent, of a transition metal catalyst and of a base, with a diborane of the general formula III

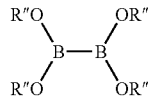

Also found has been a process for preparing substituted rylenes of the general formula Ij

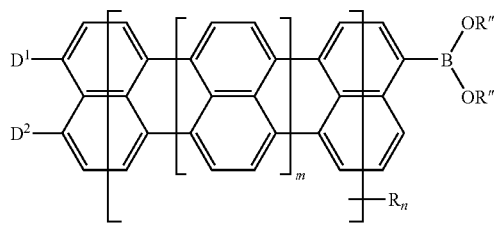

in which $D^1$ and $D^2$ are each hydrogen or one of the two $D^1$ and $D^2$ radicals is halogen or a radical of the formula (d)

and the other radical is hydrogen, which comprises a) to prepare mono(dioxaborolan-2-yl)rylenes Ij ($D^1=D^2=H$), reacting a halorylene of the general formula If

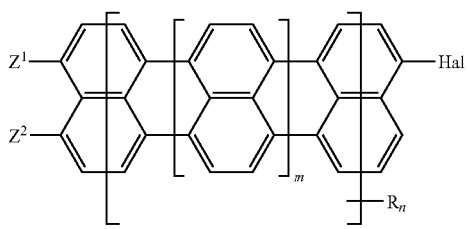

in which $Z^1$ and $Z^2$ are each hydrogen,
or
b) to prepare bis(dioxaborolan-2-yl)rylenes Ij (one of the two $D^1$ and $D^2$ radicals is a (d) radical and the other radical is hydrogen) or mixed-substituted rylenes Ij (one of the two $D^1$ and $D^2$ radicals is halogen and the other radical is hydrogen), reacting a halorylene of the formula If

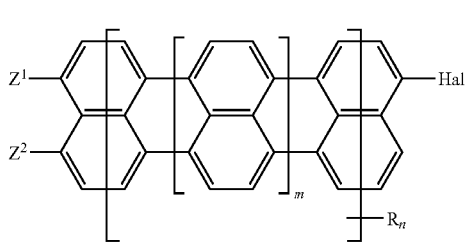

in which one of the two $Z^1$ and $Z^2$ radicals is halogen and the other radical is hydrogen,
in the presence of an aprotic organic solvent, of a transition metal catalyst and of a base, with the amount, required to introduce the total number of dioxaborolan-2-yl radicals desired, of from 1 to 3 mol, or, in the case of the mixed-substituted rylenes Ij, from 1 to 1.5 mol, of a diborane of the general formula III

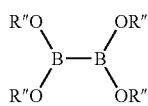

per mole of dioxaborolan-2-yl radical to be introduced.

Finally found has been a process for preparing peri-(dioxaborolan-2-yl)rylenedicarboxylic anhydrides of the general formula Ik

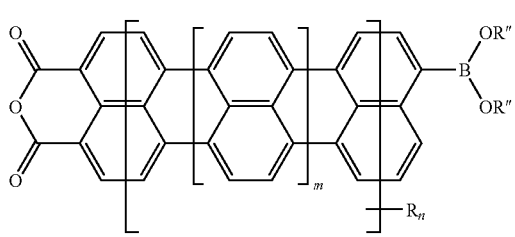

which comprises reacting a peri-halogenated rylenedicarboxylic anhydride of the general formula Ih

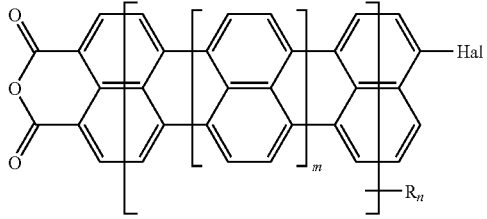

Ih in which Hal is halogen, in the presence of an aprotic organic solvent, of a transition metal catalyst and of a base, with a diborane of the general formula III

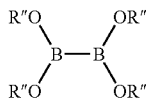

III

Additionally found has been a process for preparing symmetrical rylenetetracarboxylic acid derivatives of the general formula $Im_{cis}$ or $Im_{trans}$ $Im_{cis}$

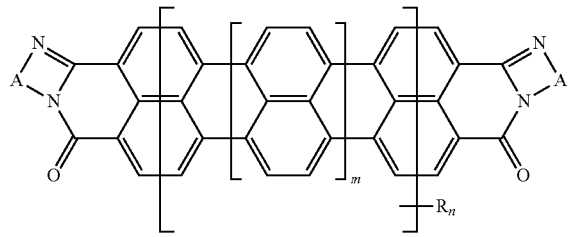

$Im_{trans}$

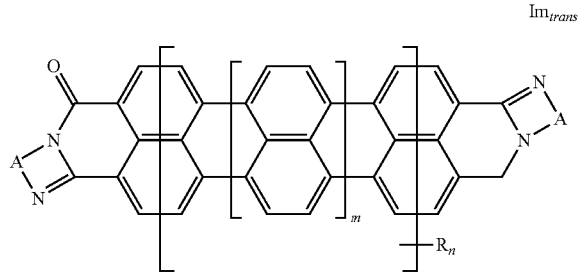

where the two A radicals are identical, or a mixture of the two isomers, which comprises condensing a rylenetetracarboxylic dianhydride of the general formula Ib

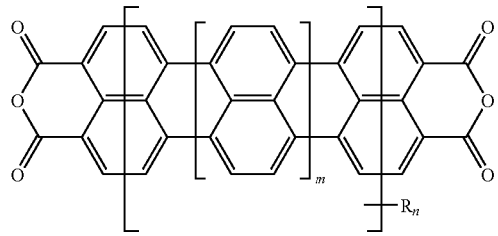

Ib in the presence of a nitrogen-basic compound or of phenol as a solvent and of a Lewis acid, or of piperazine as a catalyst, with from 2 to 3 mol/mol of an aromatic diamine of the general formula IV $$H_2N-A-NH_2 \quad \quad IV$$

Also found has been a process for preparing unsymmetrical rylenetetracarboxylic acid derivatives of the general formula $Im'_{cis}$ or $Im'_{trans}$ $Im'_{cis}$

$Im'_{trans}$

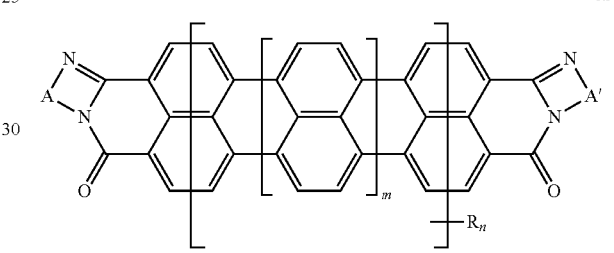

or a mixture of the two isomers, which comprises condensing a rylenetetracarboxylic dianhydride of the general formula Ib

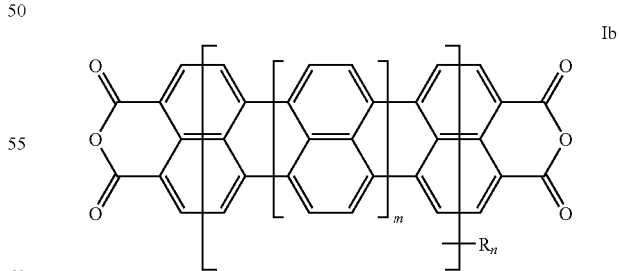

Ib in the presence of a nitrogen-basic compound or of phenol as a solvent and of a Lewis acid or of piperazine as a catalyst, first with from 1 to 1.5 mol/mol of an aromatic diamine of the general formula IV $$H_2N-A-NH_2 \quad \quad IV$$

and then with from 1 to 1.5 mol/mol of an aromatic diamine of the general formula IV'

  IV'

Additionally found has been a process for preparing rylenetetracarboxylic acid derivatives of the general formula In In

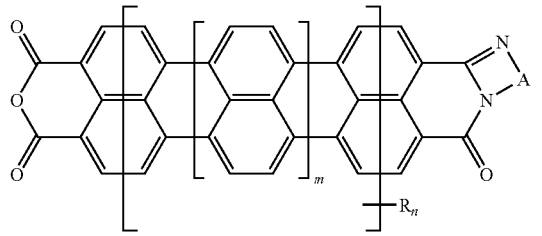

which comprises condensing a rylenetetracarboxylic dianhydride of the general formula Ib Ib

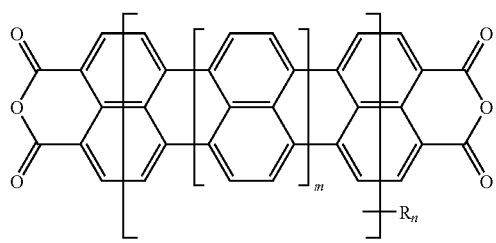

in the presence of a nitrogen-basic compound or of phenol as a solvent and of a Lewis acid or of piperazine as a catalyst, with from 1 to 1.5 mol/mol of an aromatic diamine of the general formula IV

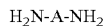  IV

Also found has been a process for preparing rylenetetracarboxylic acid derivatives of the general formula Io Io

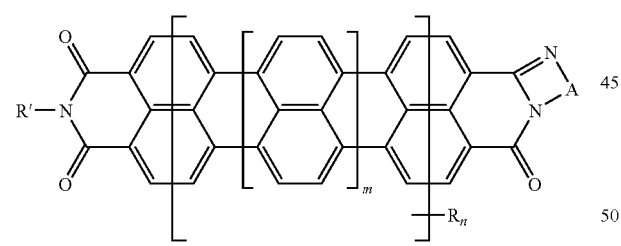

which comprises condensing a rylenetetracarboxylic monoimide monoanhydride of the general formula Ia Ia

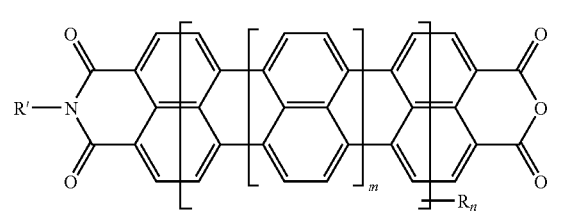

in the presence of a nitrogen-basic compound or of phenol as a solvent and of a Lewis acid or of piperazine as a catalyst, with from 1 to 1.5 mol/mol of an aromatic diamine of the general formula IV

  IV

Also found has been a process for preparing rylenedicarboxylic acid derivatives of the general formula Ip Ip

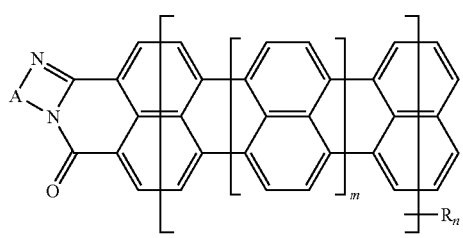

which comprises a) subjecting a rylenetetracarboxylic acid derivative of the general formula In In

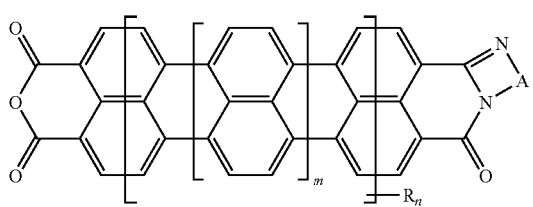

to a decarboxylation in the presence of a tertiary nitrogen-basic compound and of a transition metal catalyst or b) condensing a rylenedicarboxylic anhydride of the general formula Ig In

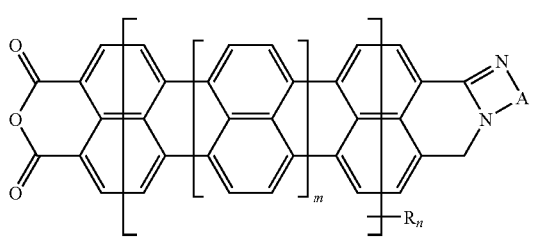

in the presence of a nitrogen-basic compound or of phenol as a solvent and of a Lewis acid or of piperazine as a catalyst, with from 1 to 1.5 mol/mol of an aromatic diamine of the general formula IV

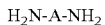   IV

Additionally found has been a process for preparing peri-halogenated rylenedicarboxylic acid derivatives of the general formula Iq

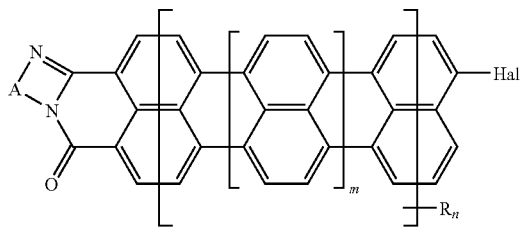

which comprises reacting a rylenedicarboxylic acid derivative of the general formula Ip

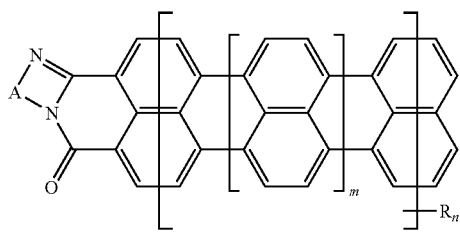

with N-halosuccinimide in the presence of a polar organic solvent and of a Lewis acid Finally found has been a process for preparing peri-(dioxaborolan-2-yl)rylenedicarboxylic acid derivatives of the general formula Ir

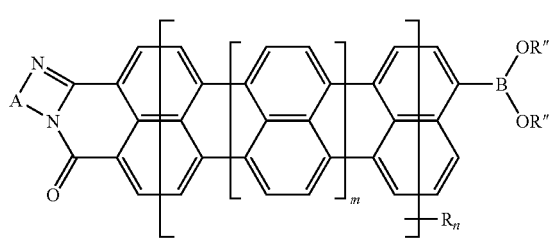

which comprises reacting a peri-halogenated rylenedicarboxylic acid derivative of the general formula Iq

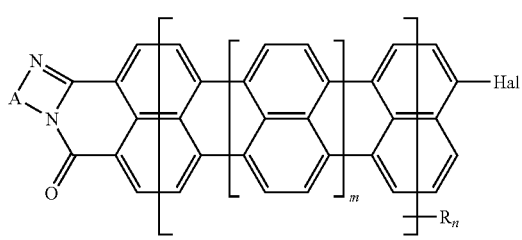

in which Hal is halogen, in the presence of an aprotic organic solvent, of a transition metal catalyst and of a base, with a diborane of the general formula III

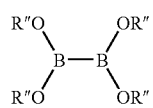

Specific examples of the R, R', R", $R^1$ to $R^3$ radicals mentioned in the formulae and their substituents are as follows:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above terms isooctyl, isononyl, isodecyl and isotridecyl are trivial terms and stem from the alcohols obtained by the oxo process);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxamidecyl and 3,6,9,12-tetra-oxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethyl-thiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-tri-thiadecyl, 3,6,9-trithiaundecyl, 3,6,9-trithiadodecyl, 3,6,9,12-tetrathiamidecyl and 3,6,9,12-tetrathiatetradecyl;

2-monomethyl- and 2-monoethylaminoethyl, 2-dimethylaminoethyl, 2- and 3-dimethyl-aminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazamidecyl and 3,6,9,12-tetramethyl-3,6,9,12-tetraazamidecyl;

(1-ethylethylidene)amino ethylene, (1-ethylethylidene)aminopropylene, (1-ethylethylidene)aminobutylene, (1-ethylethylidene)aminodecylene and (1-ethylethylidene)aminododecylene; propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulf-oxidoethyl, 2-butylsulfoxidoethyl, 2- and 3-methylsulfoxidopropyl, 2- and 3-ethylsulf-oxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 1- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxy-tetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 1-hydroxyprop-2-yl, 3- and 4-hydroxybutyl, 1-hydroxybut-2-yl and 8-hydroxy-4-oxaoctyl;

2-cyanoethyl, 3-cyanopropyl, 3- and 4-cyanobutyl, 2-methyl-3-ethyl-3-cyanopropyl, 7-cyano-7-ethylheptyl and 4,7-dimethyl-7-cyanoheptyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

methylthio, ethylthio, propylthio, isopropylthio, butylthio, isobutylthio, sec-butylthio, tert-butylthio, pentylthio, isopentylthio, neopentylthio, tert-pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, isopropylamino, butylamino, isobutylamino, pentylamino, hexylamino, dimethylamino, methylethylamino, diethylamino, dipropyl-amino, diisopropylamino, dibutylamino, diisobutylamino, dipentylamino, dihexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

aminosulfonyl, N,N-dimethylaminosulfonyl, N,N-diethylaminosulfonyl, N-methyl-N-ethylaminosulfonyl, N-methyl-N-dodecylaminosulfonyl, N-dodecylaminosulfonyl, (N,N-dimethylamino)ethylaminosulfonyl, N,N-(propoxyethyl)dodecylaminosulfonyl, N,N-diphenylaminosulfonyl, N,N-(4-tert-butylphenyl)octadecylaminosulfonyl and N,N-bis(4-chlorophenyl)aminosulfonyl;

methoxycarbonyl, ethoxycarbonyl, propoxycarbonyl, isopropoxycarbonyl, hexoxycarbonyl, dodecyloxycarbonyl, octadecyloxycarbonyl, phenoxycarbonyl, (4-tert-butylphenoxy)carbonyl and (4-chlorophenoxy)carbonyl;

methoxysulfonyl, ethoxysulfonyl, propoxysulfonyl, isopropoxysulfonyl, butoxysulfonyl, isobutoxysulfonyl, tert-butoxysulfonyl, hexoxysulfonyl, dodecyloxysulfonyl, octadecyloxysulfonyl, phenoxysulfonyl, 1- and 2-naphthyloxysulfonyl, (4-tert-butylphenoxy)sulfonyl and (4-chlorophenoxy)sulfonyl;

diphenylphosphino, di-(o-tolyl)phosphino and diphenylphosphinoxido;

chlorine, bromine and iodine;

phenylazo, 2-naphthylazo, 2-pyridylazo and 2-pyrimidylazo;

cyclopropyl, cyclobutyl, cyclopentyl, 2- and 3-methylcyclopentyl, 2- and 3-ethylcyclo-pentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 1-morpholinyl, 1-thiomorpholinyl, 2- and 3-tetrahydrofuryl, 1-, 2- and 3-pyrrolidinyl, 1-piperazyl, 1-diketopiperazyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothia-zolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methyliso-indolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydro-isoquinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethylquinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl;

2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 2- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)-aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthyl-azo)phenyl, 4-(2-pyridylazo)

phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

The inventive rylene derivatives I and the processes for their preparation which are likewise in accordance with the invention will be detailed individually hereinbelow.

The variables occurring in the formulae used here, unless stated otherwise, are each as defined at the outset.

In these formulae and also in the claims, the carboxylic acid functions are always shown in anhydride form and also referred to as anhydride. However, the free carboxylic acids or salts thereof are likewise obtainable by the procedures described or are obtained as intermediates and merely have to be isolated.

The rylenetetracarboxylic monoimide monoanhydrides Ia

Ia and the rylenetetracarboxylic dianhydrides Ib

Ib can be prepared advantageously in accordance with the invention by subjecting a rylenetetracarboximide II

II to a hydrolysis under alkaline conditions in the presence of a polar organic solvent and isolating the rylenetetracarboxylic monoimide monoanhydride Ia and the rylenetetracarboxylic dianhydride Ib, preferably by column chromatography, and separating them from one another.

It is advantageous in this procedure (variant a) of the particular individual process) that it also starts from symmetrical rylenetetracarboximides II for the preparation of the rylenetetracarboxylic monoimide monoanhydrides, and makes superfluous the complicated synthesis of the unsymmetrical rylenetetracarboximides II which are otherwise required.

Suitable reaction media for the hydrolysis are polar, in particular protic, organic solvents. Particularly suitable are aliphatic alcohols which have from 3 to 8 carbon atoms and may be unbranched, but are preferably branched. Examples include, in addition to n-propanol and n-butanol, in particular isopropanol, sec- and tert-butanol and 2-methyl-2-butanol.

It will be appreciated that it is also possible to use mixtures of solvents.

In general, from 5 to 500 ml, preferably from 20 to 100 ml, of solvent are used per g of II.

Suitable bases are alkali metal and alkaline earth metal bases, preference being given to the alkali metal bases and particular preference to the sodium and potassium bases. The bases used are both inorganic bases, in particular the hydroxides such as sodium hydroxide and potassium hydroxide, and organic bases, in particular the alkoxides such as sodium methoxide, potassium methoxide, potassium isopropoxide and potassium tert-butoxide, which are typically used in anhydrous form. Very particular preference is given to potassium hydroxide.

It will be appreciated that it is also possible to use mixtures of bases.

In general, from 10 to 200 mol, preferably from 30 to 70 mol, of base are required per mole of II.

Especially in the case of hydrolysis of terrylenetetracarboximides II, it has been found to be advantageous additionally to use a metal fluoride, in particular an alkali metal fluoride, for example potassium fluoride, sodium fluoride or lithium fluoride, as an assistant.

Suitable amounts of assistant are generally from 0.1 to 4 mol, in particular from 0.5 to 1.5 mol, per mole of base.

The reaction temperature is generally from 50 to 120° C., preferably from 60 to 100° C.

Typical reaction times are from 0.5 to 24 h, in particular from 2 to 10 h.

In terms of process technology, the procedure is appropriately as follows:

A mixture of base, if appropriate assistant and solvent is heated to the reaction temperature with vigorous stirring and then the rylenetetracarboximide II is added. After the desired reaction time, an acid, for example an inorganic acid such as hydrochloric acid or preferably an organic acid such as acetic acid, is added dropwise until a pH of from about 1 to 4 has been attained, and the mixture is stirred at the reaction temperature for a further 1 to 4 h. The reaction product precipitated by dilution with water after cooling to room temperature is filtered off, washed with hot water and dried at about 100° C. under reduced pressure.

When the corresponding carboxylic acid salt is to be isolated instead of the particular anhydride, the procedure is appropriately not to acidify the reaction mixture after the hydrolysis, but instead only to cool it to room temperature, filter off the precipitated product, wash with a lower aliphatic alcohol such as isopropanol, and dry at about 100° C. under reduced pressure.

Rylenetetracarboxylic monoimide monoanhydride Ia and rylenetetracarboxylic dianhydride Ib may be isolated by column chromatography on silica gel with toluene or chloroform as the eluent and purified, i.e. separated from one another and from unhydrolyzed reactant II.

The yield for the mixture of rylenetetracarboxylic monoimide monoanhydride Ia and rylenetetracarboxylic dianhydride Ib is typically from 70 to 90%.

Selection of suitable reaction conditions allows the reaction, if desired, also to be steered in the direction of single or of double hydrolysis (respective process variants b)).

Thus, the single hydrolysis is promoted by milder reaction conditions such as smaller amounts of base, lower reaction temperatures and shorter reaction times, while, in the case of more severe reaction conditions such as larger amounts of base, addition of assistant, higher reaction temperatures and longer reaction times, double hydrolysis predominates.

Rylenetetracarboxylic monoimide monoanhydride Ia and rylenetetracarboxylic dianhydride Ib may be obtained in this way generally in yields of from 30 to 70% (for Ia) or from 50 to 90% (for Ib).

In the inventive preparation of the rylenedicarboximides Ic

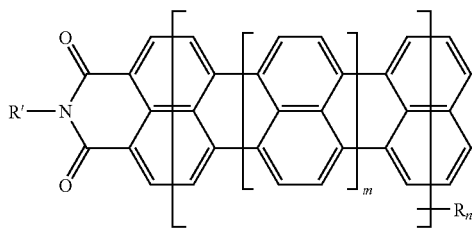

Ic and also of the rylenes Id

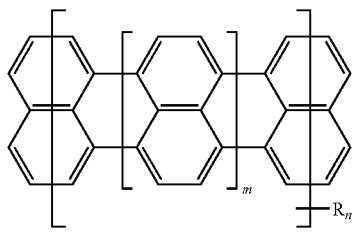

Id the mixture, obtained in the hydrolysis of the rylenetetracarboximide II, of rylenetetracarboxylic monoimide monoanhydride Ia and rylenetetracarboxylic dianhydride Ib, which typically also comprises unhydrolyzed rylenetetracarboximide II, is used and is subjected to a decarboxylation in the presence of a tertiary nitrogen-basic compound as a solvent and of a transition metal catalyst (respective process variants a)). The rylenedicarboximides Ic and rylenes Id formed here may be separated from one another readily by column chromatography.

It will be appreciated that the rylenedicarboximides Ic and the rylenes Id may also be prepared in accordance with process variants b) from the rylenetetracarboxylic monoimide monoanhydride Ia or rylenetetracarboxylic dianhydride Ib isolated in each case.

Suitable reaction media for the decarboxylation are tertiary nitrogen-basic compounds whose boiling point is preferably above the reaction temperature. Examples of particularly suitable solvents are N,N-disubstituted aliphatic carboxamides (in particular N,N-di-$C_1$-$C_4$-alkyl-$C_1$-$C_4$-carboxamides) and nitrogen heterocycles.

Specific examples include: dimethylformamide, diethylformamide, dimethylacetamide, dimethylbutyramide, N-methylpyrrolidone, 3-methylpyridine, quinoline, isoquinoline and quinaldine, preference being given to quinoline.

It will be appreciated that it is also possible to use solvent mixtures.

In general, from 5 to 200 ml, in particular from 10 to 70 ml, of solvent are used per g of reactant to be decarboxylated.

Suitable catalysts are in particular the transition metals copper and zinc and their compounds, in particular their oxides and their inorganic and organic salts which are used preferably in anhydrous form.

Examples of preferred catalysts are copper, copper(I) oxide, copper(II) oxide, copper(I) chloride, copper(II) acetate, zinc acetate and zinc propionate, particular preference being given to copper(I) oxide and zinc acetate.

It will be appreciated that it is also possible to use mixtures of the catalysts mentioned.

In general, from 0.5 to 2 mol, preferably from 0.9 to 1.2 mol, of catalyst is used per mole of reactant to be decarboxylated.

The reaction temperature is typically from 100 to 250° C., preferably from 160 to 220° C.

It is recommended to work under protective gas, for example nitrogen or argon.

The decarboxylation is complete generally within from 0.5 to 24 h, in particular from 1 to 5 h.

In process technology terms, the procedure is appropriately as follows:

A mixture of reactant to be decarboxylated, solvent and catalyst is heated with stirring under protective gas to the desired reaction temperature. After the desired reaction time and cooling to room temperature, the reaction product is precipitated in an aqueous acid, in particular dilute hydrochloric acid, and the mixture is stirred if desired at 60° C. for about 1 h. The reaction product is filtered off, washed with hot water and dried at about 100° C. under reduced pressure.

Rylenedicarboximide Ic and rylene Id may be isolated by column chromatography on silica gel with toluene as the eluent and purified, i.e. separated from one another and from unconverted reactant.

The yield for the mixture of rylenedicarboximide Ic and rylene Id is, starting from the rylenetetracarboximide II, typically from 65 to 85%.

It is also possible in the preparation of the peri-halogenated rylenedicarboximides Ie

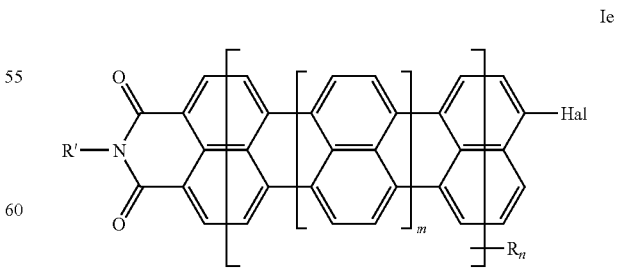

Ie (Hal: halogen, preferably chlorine, bromine or iodine, more preferably chlorine or bromine, most preferably bromine) and of the halogenated rylenes If

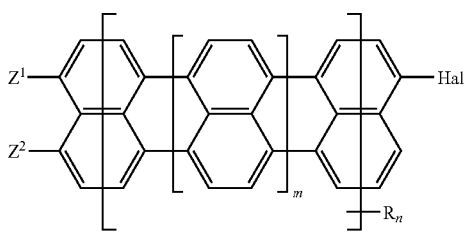

If (Hal: halogen, preferably chlorine, bromine or iodine, more preferably chlorine or bromine, most preferably bromine; $Z^1$, $Z^2$: hydrogen, or one of the $Z^1$ or $Z^2$ radicals is halogen, preferably chlorine, bromine or iodine, more preferably chlorine or bromine, most preferably bromine, and the other radical is hydrogen),
in accordance with the inventive process variant b), advantageously to use the mixture, obtained in the above-described decarboxylation, of rylenedicarboximide Ic and rylene Id, which typically also comprises unhydrolyzed rylenetetracarboximide II, which is in turn based on the mixture, obtained in the hydrolysis of the rylenetetracarboximide II, of rylenetetracarboxylic monoimide monoanhydride Ia and rylenetetracarboxylic dianhydride Ib. The resulting halogenated rylene derivatives Ie and If can be separated easily by column chromatography.

It will be appreciated that the halogenated rylene derivatives Ie and If may also be prepared by halogenating the isolated individual compounds Ic and Id (process variants a)).

The inventive halogenation is undertaken with N-halosuccinimide in the presence of a polar organic solvent and of a Lewis acid as a catalyst.

This procedure can be employed in order to prepare the chlorinated, brominated or iodinated rylene derivatives Ie and If, preference being given to the chlorinated products and particular preference to the brominated products.

The rylenedicarboximides Ic are monohalogenated regioselectively in the peri-position; the rylene derivatives Id may be mono- and dihalogenated.

In the dihalogenation of the rylene derivatives Id, the possibility exists, both in process variant a) and in process variant b) of undertaking the halogenation in one step with addition of the total amount of N-halosuccinimide required (process variants a1) and b1)).

However, a stepwise halogenation in accordance with process variants a2) and b2) may be preferable, in which the monohalogenated rylene If ($Z^1$=$Z^2$=H) is prepared in a first step and, preferably after intermediate isolation of the monohalorylene, the dihalogenated rylene If ($Z^1$ or $Z^2$=halogen) is prepared in a second step. The two-stage procedure additionally enables, by use of different N-halosuccinimides, the controlled preparation of mixed-halogenated rylenes If which are substituted on one side of the molecule (in the 3 position) by one halogen and on the other side of the molecule (correspondingly in the 11- or 12-position in terrylene and in the 13- or 14-position in quaterrylene) by the other halogen. In general, the dihalogenation always affords mixtures of the 3,11- and 3,12-dihaloterrylenes or the 3,13- and 3,14-dihaloquaterrylenes.

Suitable polar organic solvents for the halogenation are in particular aprotic solvents. Preferred examples of these solvents are the aforementioned aliphatic carboxamides such as dimethylformamide and dimethylacetamide, and halogenated hydrocarbons such as chloroform and methylene chloride. Particular preference is given to dimethylformamide.

In general, from 25 to 200 ml, preferably from 50 to 150 ml, of solvent are used per g of reactant to be halogenated.

Suitable Lewis acid catalysts are in particular metal halides, preference being given to iron(III) halides, aluminum trihalides and zinc halides. Specific examples include iron(III) chloride, iron(III) bromide, iron(III) iodide, aluminum trichloride, aluminum tribromide, aluminum triiodide and zinc chloride, particular preference being given to the iron halides.

In general, from 0.01 to 0.5 mol, preferably from 0.05 to 0.2 mol, of Lewis acid is used per mole of reactant to be halogenated.

The amount of N-halosuccinimide depends upon the degree of halogenation desired. Typically, from 1 to 6 mol, in particular from 1 to 4 mol, of N-halosuccinimide are required per halogen atom to be introduced. When mixtures of rylenedicarboximide Ic and rylene Id are used, it has to be taken into account that both reactants are to be halogenated. When the dihalorylenes If are to be prepared stepwise, appropriately from 1 to 3 mol of N-halosuccinimide are used in the first step per mole of rylene Id or per mole of rylene Id and rylenedicarboximide Ic when a reactant mixture is used, and generally a further from 1 to 6 mol, in particular from 1 to 4 mol, are used in the second step per mole of monohalogenated rylene If.

The halogenation temperature is generally from 20 to 100° C., preferably from 40 to 80° C.

It is recommended to work under protective gas, for example nitrogen or argon.

Typical reaction times are from 0.5 to 24 h, in particular from 1 to 2 h.

A convenient procedure is as follows:

A mixture of reactant to be halogenated, Lewis acid, N-halosuccinimide and solvent is heated to the desired reaction temperature with stirring under protective gas. After halogenation has ended and cooling to room temperature, the reaction product is precipitated with dilute inorganic acid, for example with dilute hydrochloric acid. The reaction product is filtered off, washed with hot water and dried at about 100° C. under reduced pressure.

The halogenated rylenedicarboximide Ie and rylene If may be isolated by column chromatography on silica gel with toluene as the eluent and purified, i.e. separated from one another and from unconverted reactant.

In the case of two-stage preparation of dihalorylenes If, the monohalorylene If isolated in this way may be subjected to a further halogenation as described above.

The yields for the peri-halogenated rylenedicarboximide Ie and the halogenated rylene If are, starting from the rylenetetracarboximide II, typically in each case from 25 to 40%.

The unhalogenated or peri-halogenated rylenedicarboxylic anhydrides Igh

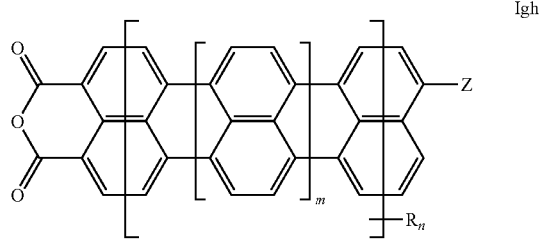

(Z: hydrogen or halogen, preferred halogen being chlorine, bromine or iodine and particularly preferred halogen being chlorine or bromine and very particularly preferred halogen being bromine)
are obtainable in accordance with the invention by hydrolyzing unhalogenated or peri-halogenated rylenedicarboximides of the general formula Ice

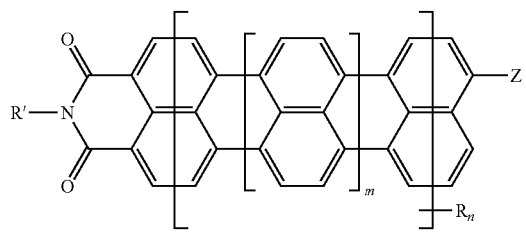

Ice

The hydrolysis may be undertaken analogously to the above-described hydrolysis of the rylenetetracarboximides II under alkaline conditions in the presence of a polar organic solvent.

Here too, especially in the case of hydrolysis of the terrylenedicarboximides Ice, the presence of a fluoride is recommended, in particular of potassium fluoride, which is used generally in amounts of from 0.1 to 2 equivalents, preferably from 0.7 to 1.3 equivalents, based on the base.

The further reaction conditions and also the process procedure correspond to the above-described hydrolysis process.

The rylenedicarboxylic acid salts or the free acid may, as described for the hydrolysis of the rylenetetracarboximide II, be isolated or prepared.

If desired, the rylenedicarboxylic anhydride Igh may be subjected to a purification by column chromatography with chloroform as the eluent, but this will generally not be required.

The yield is typically from 70 to 90% based on the rylenedicarboximide Ice used.

It will be appreciated that the peri-halogenated rylenedicarboxylic anhydrides Ih

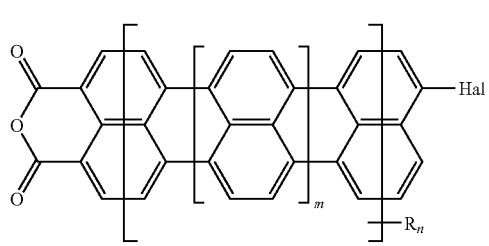

Ih (Hal: halogen, preferably chlorine, bromine or iodine, more preferably chlorine or bromine, most preferably bromine)

may also be prepared in accordance with the invention by halogenating the corresponding rylenedicarboxylic anhydride Ig

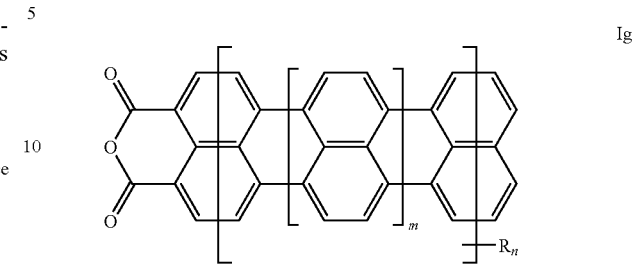

Ig

The halogenation may advantageously be undertaken with N-halosuccinimide in the presence of a polar organic solvent and of a Lewis acid as a catalyst analogously to the above-described halogenation of the rylenedicarboximides Ic and of the rylenes Id.

The peri-(dioxaborolan-2-yl)rylenedicarboximides Ii

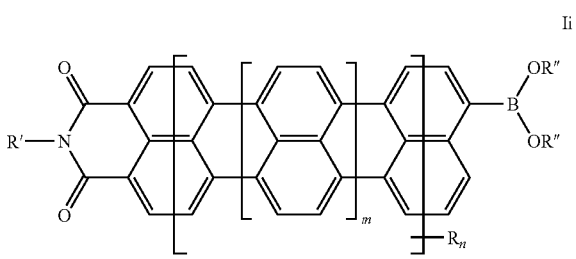

Ii and the peri-(dioxaborolan-2-yl)rylenedicarboxylic anhydrides Ik

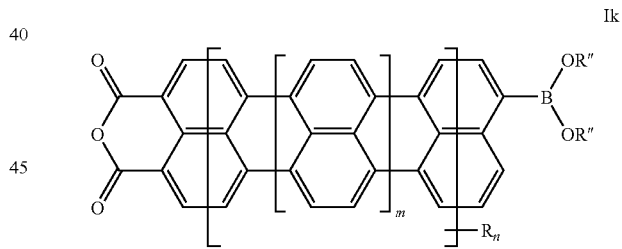

Ik are obtainable in accordance with the invention by reacting the corresponding peri-halogenated rylenedicarboximide Ie

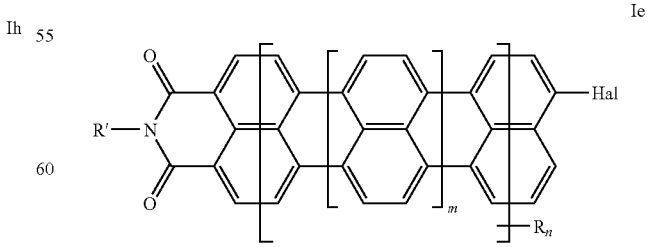

Ie (Hal: halogen, preferably chlorine, bromine or iodine, more preferably chlorine or bromine, most preferably bromine) or the peri-halogenated rylenedicarboxylic anhydride Ih

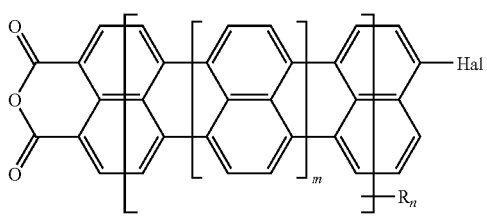

(Hal: halogen, especially preferably chlorine, bromine or iodine, more preferably chlorine or bromine, most preferably bromine)
with a diborane of the general formula III

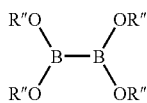

in the presence of an aprotic organic solvent, of a transition metal catalyst and of a base.

The (dioxaborolan-2-yl)-substituted rylenes Ij

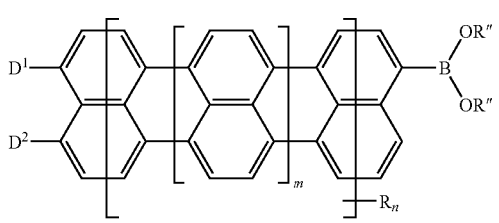

may be prepared analogously in accordance with the invention from the halorylenes If

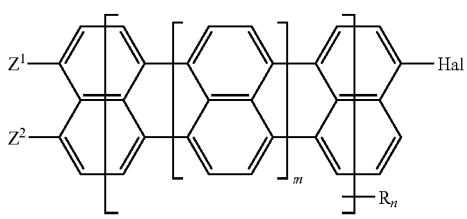

To prepare the mono(dioxaborolan-2-yl)rylenes Ij ($D^1=D^2=H$), monohalorylenes If ($Z^1=Z^2=H$) are used.

Bis(dioxaborolan-2-yl)rylenes Ij ($D^1$ or $D^2$=(d) radical)

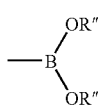

are obtainable correspondingly from the dihalorylenes If ($Z^1$ or $Z^2$=halogen).

Finally, exchange of only one of the halogen atoms present in the dihalorylene If also makes it possible to obtain mixed-substituted rylenes Ij ($D^1$ or $D^2$=halogen).

Since the dihalorylenes If are generally the above-described isomer mixtures, the (dioxaborolan-2-yl)-substituted rylenes Ij prepared from them are also obtained as isomer mixtures.

In general, a (dioxaborolan-2-yl) radical is introduced into the rylene derivative Ie, Ih and/or If by using from 1 to 3 mol, preferably from 1 to 2 mol, of diborane III per mole of rylene derivative.

When only one of the halogen atoms present in the dihalorylenes If is to be replaced by a (dioxaborolan-2-yl) radical, it is recommended to slightly lower the amount of diborane III and to use from about 1 to 1.5 mol of diborane III per mole of rylene derivative If in order to prevent double substitution.

To prepare the bis(dioxaborolan-2-yl)rylenes Ij, typically double the amount of diborane III is accordingly required.

Suitable diboranes III are in particular bis(1,2- and 1,3-diolato)diboranes, tetraalkoxy-diboranes, tetracycloalkoxy-diboranes, tetraaryloxydiboranes and tetrahetaryloxydiboranes and also their mixed forms. Examples of these compounds include: bis(pinacolato)diborane, bis(1,2-benzenediolato)diborane, bis(2,2-dimethyl-1,3-propanediolato) diborane, bis(1,1,3,3-tetramethyl-1,3-propanediolato)diborane, bis(4,5-pinandiolato)diborane, bis(tetramethoxy) diborane, bis(tetracyclopentoxy)diborane, bis(tetraphenoxy) diborane and bis(4-pyridiyloxy)diborane.

Preference is given to diboranes III in which the two R″ radicals disposed on a boron atom are joined together with formation of a five- or six-membered ring comprising the two oxygen atoms and also the boron atom. It is possible for aromatic or saturated, even bicyclic, rings having from 5 to 7 carbon atoms to be fused to the five-membered rings formed as ring members. All rings or ring systems may be substituted by up to 4 $C_1$-$C_{30}$-alkyl, $C_5$-$C_8$-cycloalkyl, aryl and/or hetaryl radicals; they are preferably substituted by up to 4 $C_1$-$C_4$-alkyl radicals. Examples of these preferred diboranes are the bis(1,2- and 1,3-diolato)diboranes already mentioned above, particular preference being given to bis(pinacolato)diborane.

Suitable solvents for this reaction are in principle all aprotic solvents which are stable toward bases under the reaction conditions and have a boiling point above the selected reaction temperature, in which the halogenated reactants Ie, If and/or Ih dissolve fully at reaction temperature and the catalysts and bases used at least partially, so that substantially homogeneous reaction conditions are present. It is possible to use either nonpolar-aprotic or polar-aprotic solvents, preference being given to the nonpolar-aprotic solvents.

Examples of preferred nonpolar-aprotic solvents are solvents which boil at >100° C. from the following groups: aliphatics (especially $C_8$-$C_{18}$-alkanes), unsubstituted, alkyl-substituted and fused cycloaliphatics (especially unsubstituted $C_7$-$C_{10}$-cycloalkanes, $C_6$-$C_8$-cycloalkanes which are substituted by from one to three $C_1$-$C_6$-alkyl groups, polycyclic saturated hydrocarbons having from 10 to 18 carbon atoms), alkyl- and cycloalkyl-substituted aromatics (especially benzene which is substituted by from one to three $C_1$-$C_6$-alkyl groups or one $C_5$-$C_8$-cycloalkyl radical) and fused aromatics which may be alkyl-substituted and/or partly hydrogenated (especially naphthalene which is substituted by from one to four $C_1$-$C_6$-alkyl groups) and also mixtures of these solvents.

Examples of particularly preferred solvents include: octane, isooctane, nonane, isononane, decane, isodecane, undecane, dodecane, hexadecane and octadecane; cycloheptane, cyclooctane, methylcyclohexane, dimethylcyclohexane, trimethylcyclohexane, ethylcyclohexane, diethylcyclohexane, propylcyclohexane, isopropylcyclohexane, dipropylcyclohexane, butylcyclohexane, tert-butylcyclohexane, methylcycloheptane and methylcyclooctane; toluene, o-, m- and p-xylene, 1,3,5-trimethylbenzene (mesitylene), 1,2,4- and 1,2,3-trimethylbenzene, ethylbenzene, propylbenzene, isopropylbenzene, butylbenzene, isobutylbenzene, tert-butylbenzene and cyclohexylbenzene; naphthalene, decahydronaphthalene (decalin), 1- and 2-methylnaphthalene and 1- and 2-ethylnaphthalene; combinations of the aforementioned solvents, as may be obtained from the high-boiling, partly or fully hydrogenated fractions of thermal and catalytic cracking processes in crude oil or naphtha processing, for example mixtures of the Exxsol® type and alkylbenzene mixtures of the Solvesso® type.

Very particularly preferred solvents are xylene (all isomers), mesitylene and in particular toluene.

Examples of suitable polar-aprotic solvents are N,N-disubstituted aliphatic carboxamides (especially N,N-di-$C_1$-$C_4$-alkyl-$C_1$-$C_4$-carboxamides) and nitrogen heterocycles which have already been listed above, and also aprotic ethers (especially cyclic ethers, diaryl ethers and di-$C_1$-$C_6$-alkyl ethers of monomeric and oligomeric $C_2$-$C_3$-alkylene glycols which may comprise up to 6 alkylene oxide units, in particular diethylene glycol di-$C_1$-$C_4$-alkyl ethers), such as:

tetrahydrofuran, dioxane, diphenyl ether, the dimethyl, diethyl, dipropyl, diisopropyl, di-n-butyl, di-sec-butyl and di-tert-butyl ethers of diethylene glycol, diethylene glycol methyl ethyl ether, the dimethyl and diethyl ethers of triethylene glycol, and triethylene glycol methyl ethyl ether.

In the case of the rylenes Id, particular preference is given to the polar-aprotic solvents, in particular dioxane and dimethylformamide; for the other reactants to be halogenated, particular preference is given to the nonpolar-aprotic solvents, in particular toluene.

The amount of solvent is generally from 10 to 1000 ml, preferably from 20 to 300 ml, per g of halogenated reactant.

Suitable transition metal catalysts are in particular palladium complexes such as tetrakis(triphenylphosphine)palladium(0), tetrakis(tris-o-tolylphosphine)palladium(0), [1,2-bis(diphenylphosphino)ethane]palladium(II) chloride, [1,1'-bis(diphenylphosphino)-ferrocene]palladium(II) chloride, bis(triethylphosphine)palladium(II) chloride, bis(tricyclohexylphosphine)palladium(II) acetate, (2,2'-bipyridyl)palladium(II) chloride, bis(triphenylphosphine)palladium(II) chloride, tris(dibenzylideneacetone)dipalladium(0), 1,5-cyclooctadienepalladium(II) chloride, bis(acetonitrile)palladium(II) chloride and bis(benzonitrile)palladium(II) chloride, preference being given to [1,1'-bis(diphenylphosphino)ferrocene]palladium(II) chloride and tetrakis(triphenylphosphine)palladium(0).

Typically, the transition metal catalyst is used in an amount of from 1 to 20 mol %, in particular from 2 to 10 mol %, based on the halogenated reactant.

The bases used are preferably the alkali metal salts, especially the sodium salts and in particular the potassium salts, of weakly organic and inorganic acids, such as sodium acetate, potassium acetate, sodium carbonate, sodium hydrogencarbonate, potassium carbonate and potassium hydrogencarbonate. Preferred bases are the acetates, in particular potassium acetate.

In general, from 1 to 5 mol, preferably from 2 to 4 mol, of base are used per mole of halogenated reactant.

The reaction temperature is typically from 20 to 180° C., in particular from 60 to 120° C.

It is recommended to work under protective gas, for example nitrogen or argon.

The reaction time is generally from 0.5 to 30 h, in particular from 1 to 20 h.

In process technology terms, the procedure is appropriately as follows:

halogenated reactant and solvent are initially charged, diborane III, the transition metal catalyst and the base are added successively and the mixture is heated to the desired reaction temperature under protective gas for from 0.5 to 30 h. After cooling to room temperature, the solid constituents are filtered off from the reaction mixture and the solvent is distilled off under reduced pressure.

The rylene derivative Ik is not obtained here in anhydride form, but rather is generally present in the form of the rylene-dicarboxylic acid salt. The anhydride itself may be obtained in a simple manner by adding an acid. In this way, a dioxaborolan-2-yl radical present as the ester (R"≠H) is hydrolyzed to the boronic acid (R"=H):

If desired, the (dioxaborolan-2-yl)-substituted rylene derivatives Ii, Ij and Ik may be subjected to a purification by column chromatography with a 2:1 mixture of chloroform and hexane as the eluent, but this will generally not be required.

The yield is typically from 80 to 100%.

The rylene derivatives I having anhydride functions (or acid functions) may be condensed with aromatic diamines IV.

The double condensation products obtainable starting from the rylenetetracarboxylic dianhydrides Ib are generally obtained in the form of mixtures of the cis isomer $Im_{cis}$ and of the trans isomer $Im_{trans}$

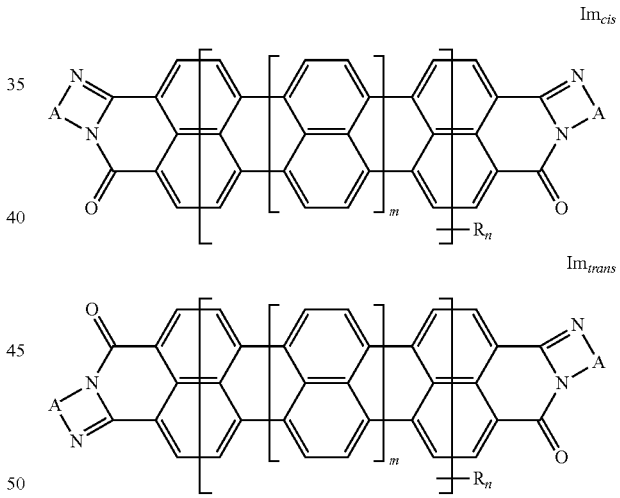

By stepwise reaction with two different diamines IV and IV', it is also possible to obtain the corresponding unsymmetrical condensation products $Im'_{cis}$ and $Im'_{trans}$

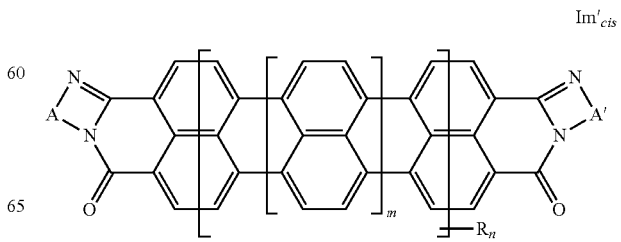

-continued

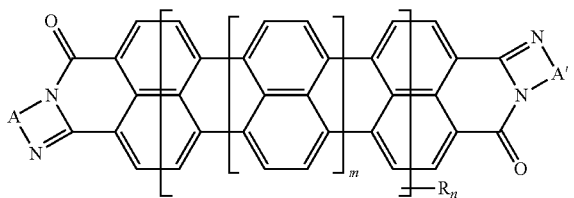

Im′$_{trans}$

However, it is also possible to subject the rylenetetracarboxylic dianhydrides Ib only to a single condensation reaction with the aromatic diamine IV, by which it is possible to obtain the rylenetetracarboxylic acid derivatives In

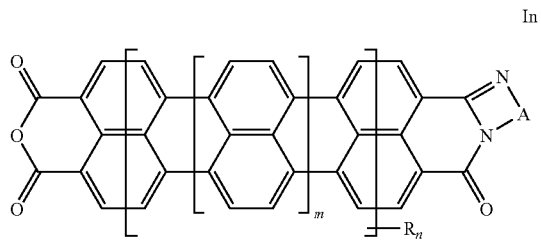

In

The rylenetetracarboxylic acid derivatives Io

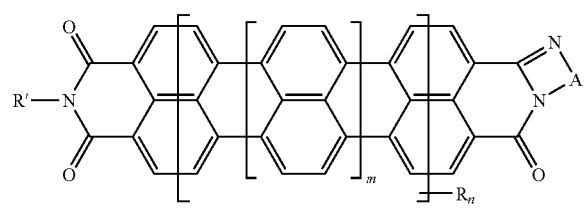

Io can be prepared by corresponding reaction of the rylenetetracarboxylic monoimide monoanhydrides Ia.

Finally, the rylenedicarboxylic acid derivatives Ip

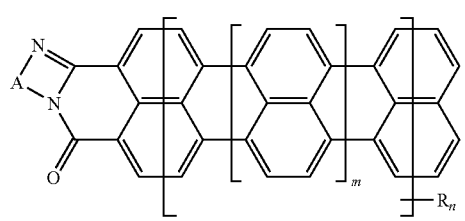

Ip may be prepared by condensing the rylenedicarboxylic anhydrides Ig with the aromatic diamines IV.

The condensation of the rylene derivatives I having anhydride functions with the aromatic diamines W is carried out in accordance with the invention in the presence of a nitrogen-basic compound or of phenol as a solvent and of a Lewis acid or of piperazine as a catalyst.

To prepare the monocondensation products, typically from 1 to 1.5 mol, preferably from 1.05 to 1.2 mol, of aromatic diamine IV are used per mole of anhydride reactant. To prepare the symmetrical dicondensation products Im, accordingly, generally from 2 to 3 mol, especially from 2.1 to 2.4 mol, of diamine IV are used.

When the unsymmetrical dicondensation products Im′ are to be prepared, it is recommended to react the rylenetetracarboxylic dianhydrides Ib first with only from 1 to 1.5 mol, in particular from 1 to 1.2 mol, of the diamine IV and then with from 1 to 1.5 mol, especially from 1 to 1.2 mol, of the diamine IV′.

Suitable aromatic diamines IV are o-phenylenediamine, 1,8-diaminonaphthalene and 3,4-diaminopyridine. The diamines may be substituted by $C_1$-$C_{12}$-alkyl, $C_1$-$C_6$-alkoxy, hydroxyl, nitro and/or halogen, but are preferably unsubstituted. Preferred diamines IV are o-phenylenediamine and 1,8-diaminonaphthalene.

Suitable nitrogen-basic compounds are in particular nitrogen heterocycles which are preferably not further functionalized, such as quinoline, isoquinoline, quinaldine, pyrimidine, N-methylpiperidine, pyridine, pyrrole, pyrazole, triazole, tetrazole, imidazole and methylimidazole. Preference is given to tertiary nitrogen-basic compounds, in particular quinoline.

In general, from 5 to 200 ml, preferably from 10 to 50 ml, of solvent are used per g of rylene derivative.

Suitable catalysts are Lewis acids, for example zinc compounds, in particular zinc salts such as zinc acetate and zinc chloride, and zinc oxide, inorganic and organic acids such as hydrochloric acid, acetic acid and p-toluenesulfonic acid, preference being given to zinc acetate.

Likewise suitable as a catalyst is piperazine which is preferably used in combination with phenol as a solvent.

Typically, from 0.25 to 5.0 mol, in particular from 1.0 to 2.0 mol, of catalyst are used per anhydride group to be converted.

The reaction temperature is generally from 100 to 240° C., preferably from 160 to 240° C.

It is recommended to work under protective gas, for example nitrogen or argon.

In general, the condensation has ended within from 0.5 to 24 h, in particular from 2 to 6 h.

In process technology terms, the procedure is appropriately as follows:

A mixture of anhydride reactant, catalyst, diamine and solvent is heated to the desired reaction temperature with stirring under protective gas. After the end of condensation and cooling to room temperature, the reaction product is precipitated with dilute hydrochloric acid, filtered off, washed with hot water and dried at about 100° C. under reduced pressure.

If desired, the resulting condensation products may be subjected to purification by column chromatography with chloroform as the eluent, but this will generally not be required.

The yield is typically from 90 to 95%.

The rylenedicarboxylic acid derivatives Ip

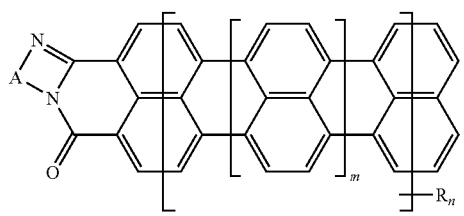

Ip are also obtainable in accordance with the invention by decarboxylating the rylenetetracarboxylic acid derivatives In

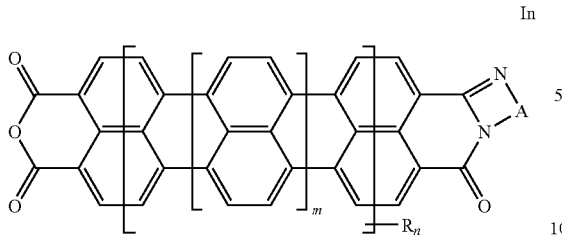

In

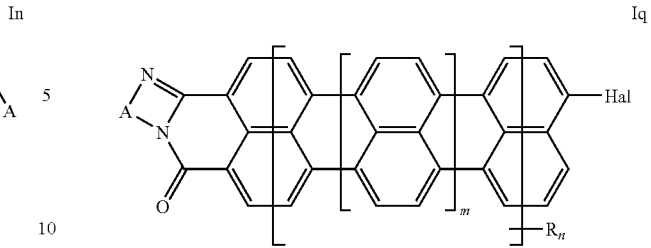

Iq

The decarboxylation is undertaken advantageously in the presence of a tertiary nitrogen-basic compound as a solvent and of a transition metal catalyst analogously to the above-described decarboxylation of rylenetetracarboxylic monoimide monoanhydride Ia and rylenetetracarboxylic dianhydride Ib.

The peri-halogenated rylenedicarboxylic acid derivatives Iq

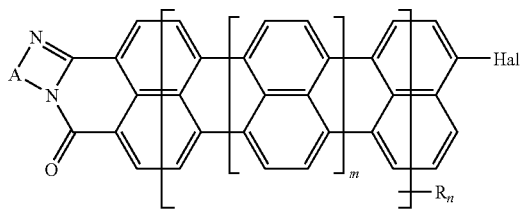

Iq (Hal: halogen, preferably chlorine, bromine or iodine, more preferably chlorine or bromine, most preferably bromine) are finally obtainable in accordance with the invention by reacting the rylenedicarboxylic acid derivatives Ip

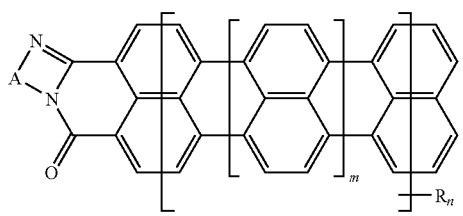

Ip with N-halosuccinimide in the presence of a polar organic solvent and of a Lewis acid as a catalyst.

In this case, it is possible to proceed analogously to the halogenation described above for the rylenedicarboximides Ic, rylenedicarboxylic anhydrides Ig and rylenes Id. The arylene or hetarylene radical may also be halogenated from one to four times.

It is also possible to obtain the peri-(dioxaborolan-2-yl) rylenedicarboxylic acid derivatives Ir

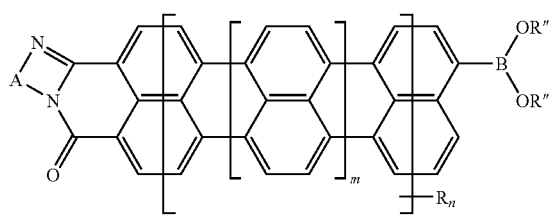

Ir in accordance with the invention by reacting the peri-halogenated rylenedicarboxylic acid derivatives Iq with an aromatic diborane III

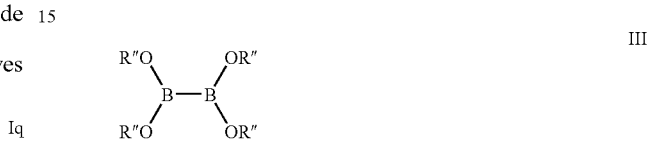

III in the presence of an aprotic organic solvent, of a transition metal catalyst and of a base.

The procedure is advantageously analogous to the above-described reaction of the peri-halogenated rylenedicarboximides Ie, of the peri-halogenated rylenedicarboxylic anhydrides Ih and of the halorylenes If with the diborane III.

The inventive rylene derivatives I exhibit strong absorption in the infrared region at wavelengths of from 550 to 900 nm. Their functionalization can be selected such that they can be adapted directly to the desired end use.

They are suitable for a multitude of applications, such as the coloring of high molecular weight organic and inorganic materials, for example of coatings, printing inks and plastics, for producing aqueous polymer dispersions which absorb in the near infrared region of the electromagnetic spectrum, for obtaining markings and inscriptions which absorb infrared light and are invisible to the human eye, as infrared absorbers for heat management, as IR laser beam-absorbing materials in the fusion treatment of plastics parts, as semiconductors in organic electronics, as emitters in electro- and chemiluminescence applications, and also as active components in photovoltaics.

They may also be used advantageously as reactants for preparing higher rylenes which absorbs at longer wavelength.

EXAMPLES

Example 1

N-(2,6-Diisopropylphenyl)-1,6,9,14-tetra[4-(1,1,3,3-tetramethylbutyl)phenoxy]terrylene-3,4:11,12-tetracarboxylic monoimide monoanhydride Ia' and 1,6,9,14-tetra[4-(1,1,3,3-tetramethylbutyl)phenoxy]terrylene-3,4:11,12-tetracarboxylic dianhydride Ib'

A mixture of 4.1 g (2.5 mmol) of N,N'-di(2,6-diisopropylphenyl)-1,6,9,14-tetra[4-(1,1,3,3-tetramethylbutyl)phenoxy]terrylene-3,4:11,12-tetracarboximide II' and 200 ml of tert-butanol was heated to 60° C. After 0.5 h, 4.2 g (75.6 mmol) of potassium hydroxide and 4.4 g (75.6 mmol) of potassium fluoride were added. The mixture was then heated to gentle reflux (about 80° C.) and stirred at this temperature for 16 h. The thin-layer chromatography analysis of a sample with toluene showed only a trace of unconverted reactant. 230 ml of 50% by weight acetic acid were then added dropwise and the mixture was stirred at 80° C. for another 1 h. The reaction product was precipitated in water, filtered off, washed with hot water and dried at 100° C. under reduced pressure. The crude product was subjected to column chromatography on silica gel first with toluene and then with acetone as the eluent.

1.40 g (37%) of Ia' in the form of a blue solid and also 1.15 g (34%) of Ib' in the form of a blue solid were obtained, which corresponds to a total yield of 71%.

Analytical Data of Ia':
Melting point: 312-314° C.;
$^1$H-NMR (500 MHz, CD$_2$Cl$_2$, 25° C.): δ=9.51 (s, 4H); 8.18 (s, 2H); 8.10 (s, 2H); 7.45-7.43 (m, 9H); 7.30 (d, 2H, J=7.9 Hz); 7.12 (d, 4H, J=13.8 Hz); 7.10 (d, 4H, J=13.8 Hz); 2.70 (m, 2H); 1.76 (d, 8H, J=15.0 Hz); 1.40 (d, 24H, J=11.0 Hz); 1.02 (d, 12H, J=6.8 Hz); 0.75 (d, 36H, J=24.0 Hz) ppm;
UV-Vis (CHCl$_3$): λ$_{max}$ (ε)=678 (108000), 622 (54000), 443 (1200) nm (M$^{-1}$ cm$^{-1}$);
Fluorescence (CHCl$_3$): λ$_{max}$=721 nm (excitation 680 nm);
MS (FD): m/z (rel. int.)=1492.9 (100%) [M$^+$].

Analytical Data of Ib':
Melting point: >360° C.;
$^1$H-NMR (500 MHz, CD$_2$Cl$_2$, 25° C.): δ=9.45 (s, 4H); 8.05 (s, 4H); 7.47 (d, J=8.7 Hz, 8H); 7.10 (d, J=8.9 Hz, 8H); 1.78 (d, J=8.9 Hz, 8H); 1.41 (s, 24H); 0.78 (s, 36H) ppm;
UV-Vis (CHCl$_3$): λ$_{max}$(ε)=679 (99000), 623 (50000), 444 (13000) nm (M$^{-1}$ cm$^{-1}$);
Fluorescence (CHCl$_3$): λ$_{max}$=714 nm (excitation 680 nm);
MS (FD): m/z (rel. int.)=1333.7 (100%) [M$^+$].

Example 1a 1,6,9,14-Tetra[4-1,1,3,3-tetramethylbutyl)phenoxy]terrylene-3,4:11,12-tetracarboxylic acid tetrapotassium salt Ib'''

A mixture of 2.5 g (2.1 mmol) of II' and 70 ml of tert-butanol was heated to 60° C. After 0.5 h, 3.6 g (62.3 mmol) of potassium hydroxide and 3.6 g (62.3 mmol) of potassium fluoride were added. The mixture was then heated to gentle reflux (about 80° C.) and stirred at this temperature for 18 h. The thin-layer chromatography analysis of a sample with toluene showed only a trace of unconverted reactant. The reaction product was precipitated in water, filtered off, washed with water and dried at 100° C. under reduced pressure.

29 g of Ib''' were obtained in the form of a violet solid, which corresponds to a yield of 85%.

Analytical Data of Ib''':
UV-Vis (H$_2$O): λ$_{max}$=590, 546 nm.

Example 2

N-(2,6-Diisopropylphenyl)-1,6,9,14-tetra[4-(1,1,3,3-tetramethylbutyl)phenoxy]terrylene-3,4-dicarboximide Ic' and 1,6,9,14-tetra[4-(1,1,3,3-tetramethylbutyl)phenoxy]terrylene Id'

5.44 g (37.9 mmol) of copper(I) oxide were added to a mixture, stirred under nitrogen, of 3.43 g of a reaction mixture which was obtained analogously to Example 1 and consists substantially of Ia' and Ib', and 215 ml of quinoline. The mixture was then heated to 210° C. and stirred at this temperature for 2 h. After checking the completeness of conversion by thin-layer chromatography and cooling to room temperature, the reaction product was precipitated in 1400 g of 6% by weight hydrochloric acid, filtered off, washed with hot water and dried at 100° C. under reduced pressure. The crude product was subjected to column chromatography on silica gel with a methylene chloride/hexane mixture (1:1) as the eluent.

1.32 g (yield 37%, based on the II' used in Example 1) of Ic' were obtained in the form of a blue solid, and also 1.17 g (yield 39% based on the II' used in Example 1) of Id' in the form of a red solid, which corresponds to a total yield of 76% based on the II' used in Example 1.

Analytical Data of Ic':
Melting point: 264-266° C.;
$^1$H-NMR (500 MHz, CD$_2$Cl$_2$, 25° C.): δ=9.39 (d, 2H, J=9.0 Hz); 9.17 (d, 2H, J=9.0 Hz); 8.18 (s, 2H); 7.72 (d, 2H, J=9.0 Hz); 7.45 (m, 1H); 7.40 (m, 8H); 7.30 (d, 2H, J=7.5 Hz); 7.18 (d, 2H, J=9.0 Hz); 7.08 (d, 4H, J=9.0 Hz); 7.03 (d, 4H, J=9.0 Hz); 2.68 (m, 2H); 1.73 (d, 8H, J=11.0 Hz); 1.36 (s, 24H); 1.08 (d, 12H, J=7.0 Hz); 0.75 (d, 36H, J=14.5 Hz) ppm;
UV-Vis (CHCl$_3$): λ$_{max}$ (ε)=639 (67900), 424 (8000), 394 (8100) nm (M$^{-1}$ cm$^{-1}$);
Fluorescence (CHCl$_3$): λ$_{max}$=760 nm (excitation 650 nm);
MS (FD): m/z (rel. int.)=1422.8 (100%) [M$^+$].

Analytical Data of Id':
Melting point: 280-282° C.;
$^1$H-NMR (500 MHz, CD$_2$Cl$_2$, 25° C.): δ=8.94 (s, 4H); 7.61 (d, 4H, J=8.5 Hz); 7.45 (d, 8H, J=9.0 Hz); 7.10 (d, 4H, J=8.5 Hz); 6.95 (d, 8H, J=9.0 Hz); 1.72 (s, 8H); 1.35 (d, 24H, J=11.0 Hz); 0.72 (s, 36H) ppm;
UV-Vis (CHCl$_3$): λ$_{max}$ (ε)=550 (47500), 509 (29400), 476 (11100) nm (M$^{-1}$ cm$^{-1}$);
Fluorescence (CHCl$_3$): λ$_{max}$=574 nm (excitation 550 nm);
MS (FD): m/z (rel. int.)=1192.6 (100%) [M$^+$].

Example 3

N-(2,6-Diisopropylphenyl)-1,6,9,14-tetra[4-(1,1,3,3-tetramethylbutyl)phenoxy]-11-bromoterrylene-3,4-dicarboximide Ie'

0.12 g (0.84 mmol) of N-bromosuccinimide and 0.02 g (0.08 mmol) of iron(III) bromide were added to a mixture, stirred under nitrogen, of 0.3 g (0.21 mmol) of Ic' and 42 ml of dimethylformamide. The mixture was then heated to 40° C. and stirred at this temperature for 1 h. The reaction product was precipitated in a water/hydrochloric acid mixture (80 ml/20 g), filtered off, washed with hot water and dried at 70° C. under reduced pressure. The crude product was subjected to a column filtration on silica gel with toluene.

0.21 g of Ie' was obtained in the form of a blue solid, which corresponds to a yield of 66%.

Analytical Data of Ie':
Melting point: 120-122° C.;
$^1$H-NMR (500 MHz, CD$_2$Cl$_2$, 25° C.): δ=9.40 (m, 2H); 9.16 (d, 2H, J=9.0 Hz); 9.10 (d, 2H, J=9.0 Hz); 8.18 (s, 1H); 8.17 (s, 1H); 8.08 (d, 1H, J=9.0 Hz); 7.45-7.39 (m, 10H); 7.30 (d, 2H, J=8.0 Hz); 7.22 (d, 1H, J=9.0 Hz); 7.09-7.02 (m, 8H); 2.68 (m, 2H); 1.76 (m, 8H); 1.38 (d, 24H, J=7.0 Hz); 1.07 (d, 12H, J=6.5 Hz); 0.75 (m, 36H) ppm;
UV-Vis (CHCl$_3$): λ$_{max}$ (ε)=639 (69700), 424 (8100), 394 (8200) nm (M$^{-1}$ cm$^{-1}$);
Fluorescence (CHCl$_3$): λ$_{max}$=730 nm (excitation 650 nm);
MS (FD): m/z (rel. int.)=1499.8 (100%) [M$^+$].

Example 4

1,6,9,14-Tetra[4-(1,1,3,3-tetramethylbutyl)phenoxy]-3-bromoterrylene If' and 1,6,9,14-tetra[4-(1,1,3,3-tetramethylbutyl)phenoxy]-3,11-dibromoterrylene If''

0.9 g (5.04 mmol) of N-bromosuccinimide and 0.05 g (0.17 mmol) of iron(III) bromide were added to a mixture, stirred under nitrogen, of 0.25 g (0.21 mmol) of Id' and 25 ml of dimethylformamide. The mixture was then heated to 40° C. and stirred at this temperature for 1 h. The reaction product was precipitated in a water/hydrochloric acid mixture (80 ml/20 g), filtered off, washed with hot water and dried at 75° C. under reduced pressure. The crude product was subjected to a column filtration on silica gel with a chloroform/ethyl acetate mixture (90:10).

0.05 g (19%) of If was obtained in the form of a violet solid, and also 0.07 g (25%) of If" in the form of a violet solid, which corresponds to a total yield of 44%.

Analytical Data of If':
MS (FD): m/z (rel. int.)=1351.5 (100%) [M$^+$].
Analytical Data of If":
MS (FD): m/z (rel. int.)=1272.4 (100%) [M$^+$].

Example 5

1,6,9,14-Tetra[4-(1,1,3,3-tetramethylbutyl)phenoxy]-11-bromoterrylene-3,4-dicarboxylic anhydride Ih'

A mixture of 0.13 g (0.09 mmol) of Ie' and 20 ml of tert-butanol was heated to 55° C. After 0.5 h, 0.15 g (2.7 mmol) of potassium hydroxide and 0.15 g (2.7 mmol) of potassium fluoride were added. The mixture was then heated to gentle reflux (about 80° C.) and stirred at this temperature for 16 h. The thin-layer chromatography analysis of a sample with toluene showed only a trace of unconverted reactant. The mixture was then acidified with 50% by weight acetic acid and stirred at 80° C. for another 2 h. The reaction product was precipitated in water, filtered off, washed with hot water and dried at 100° C. under reduced pressure. The crude product was subjected to column chromatography on silica gel with chloroform as the eluent.

0.09 g of Ih' was obtained in the form of a blue solid, which corresponds to a yield of 75%.

Analytical Data of Ich':
UV-Vis (CHCl$_3$): $\lambda_{max}$ ($\epsilon$) 650 (43000), 423 (6000), 399 (6700) nm (M$^{-1}$ cm$^{-1}$);
MS (FD): m/z (rel. int.)=1340.7 (100%) [M$^+$].

Example 6

N-(2,6-Diisopropylphenyl)-1,6,9,14-tetra[4-(1,1,3,3-tetramethylbutyl)phenoxy]-11-(4,4,5,5-tetramethyl-1,3,2-dioxaboran-2-yl)terrylene-3,4-dicarboximide Ii'

0.13 g (0.50 mmol) of bis(pinacolato)diboran, 0.08 g (0.8 mmol) of sodium acetate and 0.08 g (0.10 mmol) of [1,1'-bis(diphenylphosphino)ferrocene]palladium(II) chloride were added successively to a solution of 0.3 g (0.2 mmol) of Ie' in 10 ml of toluene in a 50 ml Schlenk tube. The mixture was then heated to 70° C. under argon and kept at this temperature overnight. After cooling to room temperature, the product was extracted with methylene chloride and washed with water. The solvent was then distilled off. The solid residue was subjected to a column filtration on silica gel with a chloroform/hexane:mixture (2:1) as the eluent.

0.23 g of Ii' was obtained in the form of a blue solid, which corresponds to a yield of 75%.

Analytical Data of Ii':
$^1$H-NMR (500 MHz, CD$_2$Cl$_2$, 25° C.): δ=9.39 (d, 1H, J=9.0 Hz); 9.36 (d, 1H, J=9.0 Hz); 9.14 (d, 2H, J=9.0 Hz); 8.67 (d, 1H, J=9.0 Hz); 8.18 (s, 1H); 8.15 (s, 1H); 7.50-7.35 (m, 10H); 7.29 (d, 2H, J=7.5 Hz); 7.19 (d, 1H, J=9.0 Hz); 7.07 (m, 4H); 7.02 (m, 4H); 2.68 (m, 2H); 1.73 (m, 8H); 1.36 (d, 24H, J=11.0 Hz); 1.26 (s, 12H); 1.08 (m, 12H); 0.72 (d, 36H, J=24.0 Hz) ppm;
UV-Vis (CHCl$_3$): $\lambda_{max}$=645, 424, 396 nm;
Fluorescence (CHCl$_3$): $\lambda_{max}$=750 nm (excitation 660 nm);
MS (FD): m/z (rel. int.)=1547.9 (100%) [M$^+$].

Example 7

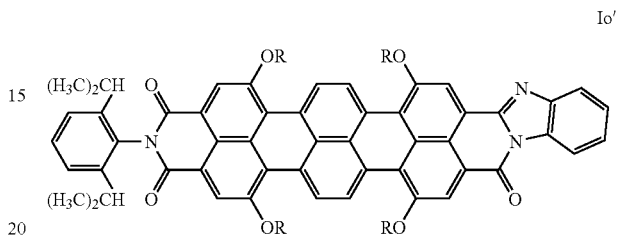

R=4-(1,1,3,3-tetramethylbutyl)phenyl

A mixture of 0.33 g (0.22 mmol) of Ia', 0.03 g (0.27 mmol) of o-phenylenediamine, 0.05 g (0.27 mmol) of zinc acetate dihydrate and 30 ml of quinoline was stirred under nitrogen for 10 min, then heated to 220° C. and stirred at this temperature for 2 h. After cooling to room temperature, the reaction product was precipitated by adding 200 ml of 5% by weight hydrochloric acid, filtered off, washed to neutrality with water and dried at 70° C. under reduced pressure. The crude product was subjected to a column filtration on silica gel with chloroform as the eluent.

0.30 g of Io' was obtained in the form of a blue-green solid, which corresponds to a yield of 87%.

Analytical Data of Io':
UV-Vis (H$_2$SO$_4$): $\lambda_{max}$ ($\epsilon$)=747 (42100), 701 (45900) nm (M$^{-1}$ cm$^{-1}$);
MS (FD): m/z (rel. int.)=1564.9 (100%) [M$^+$].

Example 8

N-(2,6-Diisopropylphenyl)-1,6,11,16-tetra[4-(1,1,3,3-tetramethylbutyl)phenoxy]quaterrylene-3,4:13,14-tetracarboxylic monoimide monoanhydride Ia" and 1,6,11,16-tetra[4-(1,1,3,3-tetramethylbutyl)phenoxy]quaterrylene-3,4:13,14-tetracarboxylic dianhydride Ib"

A mixture of 5.0 g (2.8 mmol) of N,N'-di(2,6-diisopropylphenyl)-1,6,11,16-tetra[4-(1,1,3,3-tetramethylbutyl)phenoxy]quaterrylene-3,4:13,14-tetracarboximide II", 7.2 g (112.5 mmol) of potassium hydroxide and 250 ml of tert-butanol was heated to 80° C. and stirred at this temperature for 7 h. After checking the completeness of conversion by thin-layer chromatography, the reaction mixture was admixed at 75° C. within 20 min with a solution of 33.8 g of glacial acetic acid in 170 ml of water (corresponds to about 17% by weight of acetic acid), then heated to about 90° C. and stirred at this temperature for another 4 h. The reaction product was precipitated by adding 250 ml of water, filtered off at 50° C., washed first with hot water and then repeatedly with methanol, and dried at 60° C. under reduced pressure. The crude product was subjected to column chromatography on silica gel first with toluene and then with acetone as the eluent.

1.92 g (40%) of Ia" were obtained in the form of a green solid, and also 1.26 g (31%) of Ib" in the form of a green solid, which corresponds to a total yield of 70%.

An analogous procedure, but with hydrolysis with 50% by weight acetic acid, afforded 0.51 g (10%) of Ia" and 2.85 g (70%) of Ib", which corresponds to a total yield of 80%.

Analytical Data of Ia":

$^1$H-NMR (500 MHz, $CD_2Cl_2$, 25° C.): δ=9.0 (s, 2H); 8.75 (s, 2H); 8.12 (s, 2H); 7.7 (s, 3H); 7.45-7.43 (m, 13H); 7.1 (d, 6H); 6.7 (d, 4H); 2.70 (m, 2H); 1.76 (d, 8H); 1.40 (d, 24); 1.02 (d, 12H); 0.75 (d, 36H) ppm;

UV-Vis ($CHCl_3$): $\lambda_{max}$=784, 718, 384 nm;

MS (FD): m/z (rel. int.)=1617 (100%) [M$^+$].

Analytical Data for Ib":

$^1$H-NMR (500 MHz, $CD_2Cl_2$, 25° C.): δ=9.5 (s, 4H); 8.45 (s, 4H); 8.1 (s, 4H); 7.45 (d, 8H); 7.10 (d, 8H); 1.78 (d, 8H); 1.41 (s, 24H); 0.78 (s, 36H) ppm;

UV-Vis ($CHCl_3$): $\lambda_{max}$=790, 720 nm;

MS (FD): m/z (rel. int.)=1457 (100%) [M$^+$].

Example 9

N-(2,6-Diisopropylphenyl)-1,6,11,16-tetra[4-(1,1,3,3-tetramethylbutyl)phenoxy]quaterrylene-3,4-dicarboximide Ic" and 1,6,11,16-tetra[4-(1,1,3,3-tetramethylbutyl)-phenoxy]quaterrylene Id"

0.4 g (2.7 mmol) of copper(I) oxide was added to a mixture, stirred under nitrogen, of 4.4 g of a reaction mixture which was obtained analogously to Example 8 and consists substantially of Ia" and Ib", and 50 ml of quinoline. The mixture was then heated to 210° C. and stirred at this temperature for 1 h. After cooling to room temperature, addition of 200 ml of 1 M hydrochloric acid to precipitate the reaction product, reheating to 60° C. and stirring at this temperature for 1 hour, the reaction product was filtered off, washed with hot water and then dissolved in methylene chloride. The resulting solution was dried over magnesium sulfate, removed from it and concentrated. The crude product was dissolved in toluene and fractionated by chromatography on silica gel. The resulting fractions were concentrated on a rotary evaporator and dried at 70° C. under reduced pressure.

1.55 g (36% based on the II" used in Example 8) of Ic" were obtained in the form of a green solid, and also 1.25 g (34% based on the II" used in Example 8) of Id" in the form of a blue solid, which corresponds to a total yield of 70% based on the II" used in Example 8.

Analytical Data of Ic":

$^1$H-NMR (500 MHz, $CD_2Cl_2$, 25° C.): δ=9.35 (d, 2H); 9.2 (d, 2H); 8.25 (d, 2H); 8.15 (s, 2H); 8.12 (d, 2H); 7.9 (s, 2H); 7.5 (m, 9H); 7.25 (d, 2H); 7.15 (dd, 8H); 2.70 (m, 2H); 1.76 (d, 8H); 1.40 (d, 24); 1.02 (d, 12H); 0.75 (d, 36H) ppm;

UV-Vis ($CHCl_3$): $\lambda_{max}$=738, 430, 352 nm;

MS (FD): m/z (rel. int.)=1545 (100%) [M$^+$].

Analytical Data of Id":

UV-Vis ($CHCl_3$): $\lambda_{max}$=660, 604, 558 nm;

MS (FD): m/z (rel. int.)=1317 (100%) [M$^+$].

Example 10

N-(2,6-Diisopropylphenyl)-1,6,11,16-tetra[4-(1,1,3,3-tetramethylbutyl)phenoxy]-13-chloroquaterrylene-3,4-dicarboximide Ie"

0.1 g (0.5 mmol) of N-bromosuccinimide and 0.002 g (0.01 mmol) of iron(III) chloride were added to a mixture, stirred under nitrogen, of 0.2 g (0.12 mmol) of Ic" and 10 ml of dimethylformamide. The mixture was then heated to 60° C. and stirred at this temperature for 1 h. After cooling to room temperature, the reaction product was precipitated into 100 ml of 1 M sodium hydroxide solution and extracted from the precipitate with methyl tert-butyl ether. The organic phase was dried over magnesium sulfate, removed from it and concentrated. The product was dissolved in methylene chloride and freed of impurities by filtration on silica gel.

0.08 g of Ie" was obtained in the form of a green solid, which corresponds to a yield of 42%.

Analytical Data of Ie":

$^1$H-NMR (500 MHz, $CD_2Cl_2$, 25° C.): δ=9.05 (d, 2H); 8.75 (d, 1H); 8.65 (d, 1H); 8.19 (s, 1H); 8.14 (s, 1H); 7.9 (s, 2H); 7.5 (m, 9H); 7.25 (d, 2H); 7.15 (dd, 1H); 2.70 (m, 2H); 1.76 (d, 8H); 1.40 (d, 24); 1.02 (d, 12H); 0.75 (d, 36H) ppm;

UV-Vis ($CHCl_3$): $\lambda_{max}$=676, 742 nm;

MS (FD): m/z (rel. int.)=1580 (100%) [M$^+$].

Example 11

1,6,11,16-Tetra[4-(1,1,3,3-tetramethylbutyl)phenoxy]quaterrylene-3,4-dicarboxylic anhydride Ig'

A mixture of 5.0 g (3.2 mmol) of Ic", 7.2 g (112.5 mmol) of potassium hydroxide and 250 ml of tert-butanol was heated to 80° C. and stirred at this temperature for 7 h. After checking the completeness of conversion by thin-layer chromatography, the reaction mixture was admixed at 75° C. within 20 min with a solution of 33.8 g of glacial acetic acid in 170 ml of water (corresponds to about 17% by weight acetic acid), then heated to about 90° C. and stirred at this temperature for another 4 h. The reaction product was precipitated by adding 250 ml of water, filtered off at 50° C., washed first with hot water and then repeatedly with methanol, and dried at 60° C. under reduced pressure. The crude product was subjected to column chromatography on silica gel with chloroform as the eluent.

2.6 g of Ig' were obtained in the form of a green solid, which corresponds to a yield of 60%.

Analytical Data of Ig':

UV-Vis ($CHCl_3$): $\lambda_{max}$=628, 687 nm;

MS (FD): m/z (rel. int.)=1317 (100%) [M$^+$].

Example 12

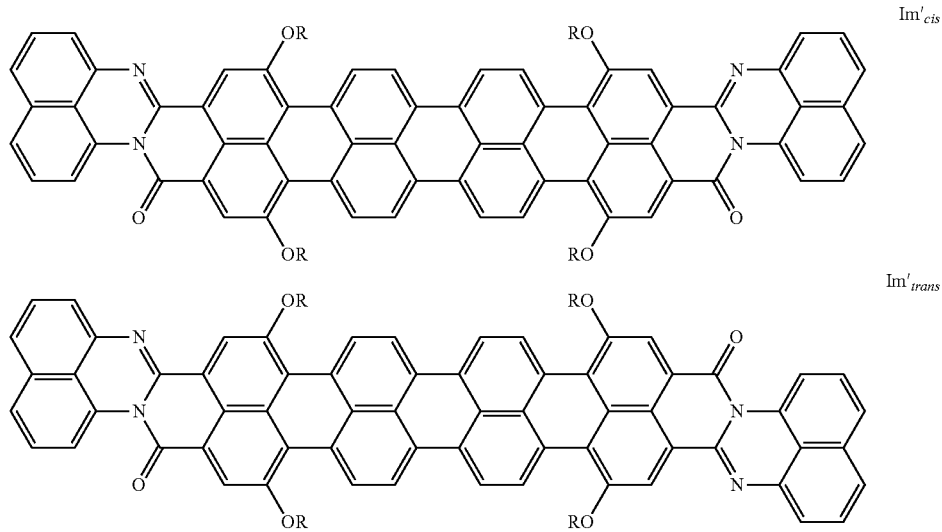

R=4-(1,1,3,3-tetramethylbutyl)phenyl

A mixture of 1.0 g (0.68 mmol) of Ib'', 0.4 g (2.4 mmol) of 1,8-diaminonaphthalene, 0.2 g (1.3 mmol) of zinc acetate dihydrate and 20 ml of quinoline was stirred under nitrogen for 10 min, then heated to 220° C. and stirred at this temperature for 4 h. After checking the completeness of conversion by thin-layer chromatography and cooling to room temperature, the reaction product was precipitated by adding 200 ml of 5% by weight hydrochloric acid, filtered off, washed to neutrality with water and dried at 70° C. under reduced pressure.

1.1 g of the cis/trans isomer mixture Im'$_{cis}$ and Im'$_{trans}$ were obtained, which corresponds to a yield of 98%.

Analytical Data:
UV-Vis (H$_2$SO$_4$): λ$_{max}$=962 nm;
MS (FD): m/z (rel. int.)=1700 (100%) [M$^+$].

Example 13

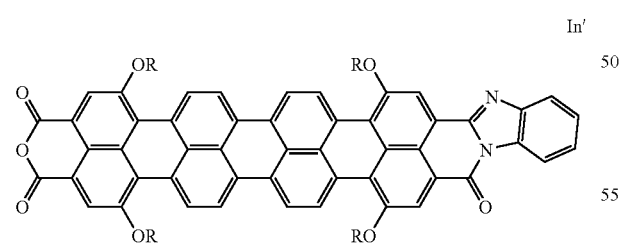

R=4-(1,1,3,3-tetramethylbutyl)phenyl

A mixture of 0.5 g (0.34 mmol) of Ib'', 0.04 g (0.37 mmol) of o-phenylenediamine, 0.06 g (0.37 mmol) of zinc acetate dihydrate and 20 ml of quinoline was stirred under nitrogen for 10 min, then heated to 215° C. and stirred at this temperature for 2 h. After cooling to room temperature, the reaction product was precipitated by adding 200 ml of 5% by weight hydrochloric acid, filtered off, washed to neutrality with water and dried at 70° C. under reduced pressure.

0.15 g of In' was obtained, which corresponds to a yield of 30%.

Analytical Data:
UV-Vis (H$_2$SO$_4$): λ$_{max}$=733, 791 nm;
MS (FD): m/z (rel. int.)=1528 (100%) [M$^+$].

The invention claimed is:

1. A process for preparing a rylenetetracarboxylic dianhydride, or a salt thereof having formula Ib

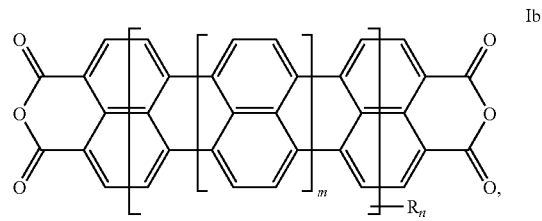

wherein
R is phenoxy, phenylthio, pyridyloxy, pyrimidyloxy, pyridylthio or pyrimidyl-thio, each of which may optionally be mono- or polysubstituted by $C_1$-$C_{12}$-alkyl, $C_1$-$C_{12}$-alkoxy and/or aryl;
m is 1 or 2;
n is 4 when m=1; 4 or 6 when m=2,
the process comprising
a) subjecting a rylenetetracarboximide of general formula II

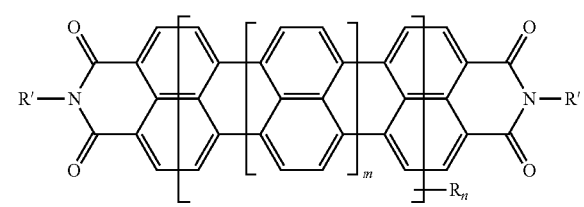

wherein R, m and n are as defined above and R' is hydrogen or a $C_1$-$C_{30}$-alkyl whose carbon chain may, optionally, be interrupted by one or more —O— and/or —CO— moieties and which may, optionally, be mono- or polysubstituted by: $C_1$-$C_6$-alkoxy, cyano and/or aryl which may, optionally, be mono- or polysubstituted by $C_1$-$C_{18}$-alkyl or $C_1$-$C_6$-alkoxy; or phenyl, or naphthyl, or pyridyl, or pyrimidyl, each of which may be, optionally, mono or polysubstituted by: $C_1$-$C_{18}$-alkyl, $C_1$-$C_6$-alkoxy, halogen, cyano, nitro, —$CONR^2R^3$, —$SO_2NR^2R^3$, or phenyl or naphthylazo, each of which may be, optionally, mono- or polysubstituted by $C_1$-$C_{10}$-alkyl, $C_1$-$C_6$-alkoxy and/or cyano; or $C_5$-$C_8$-cycloalkyl which, optionally, may be mono- or polysubstituted by $C_1$-$C_6$-alkyl, where $R^2$ and $R^3$ are each independently hydrogen; $C_1$-$C_{18}$-alkyl whose carbon chain may be interrupted by one or more —O—, —S—, —CO—, —SO— and/or —$SO_2$— moieties and which may be mono- or polysubstituted by $C_1$-$C_{12}$-alkoxy, $C_1$-$C_6$-alkylthio, hydroxyl, mercapto, halogen, cyano, nitro and/or —$COOR^1$; aryl or hetaryl to each of which may be fused further saturated or unsaturated 5- to 7-membered rings whose carbon skeleton may be interrupted by one or more —O—, —S—, —CO— and/or —$SO_2$— moieties, where the entire ring system may be mono- or polysubstituted by $C_1$-$C_{12}$-alkyl and/or the above radicals specified as substituents for alkyl; and $R^1$ is hydrogen or $C_1$-$C_{18}$-alkyl, where the $R^1$ radicals may be the same or different when they occur more than once;

to a hydrolysis under alkaline conditions in the presence of a polar organic solvent and removing the rylenetetracarboxylic dianhydride Ib from any rylenetetracarboxylic monoimide monoanhydride of formula Ia which is formed Ia

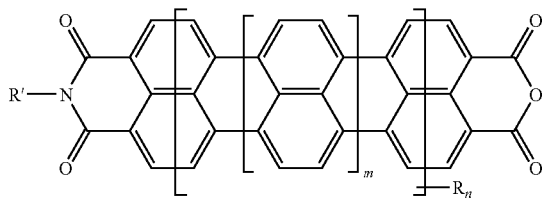

where R', R, n and m have the same meanings as above, to form the rylenetetracarboxylic dianhydride, or the salt thereof having formula Ib or b) hydrolyzing the rylenetetracarboximide of general formula II under conditions that form the compound of formula Ib and substantially no rylenetetracarboxylic monoimide monoanhydride of the formula Ia.

2. The process for preparing a rylenetetracarboxylic dianhydride, or a salt thereof having formula Ib as claimed in claim 1, wherein R is phenylthio, pyridyloxy, pyrimidyloxy, pyridylthio or pyrimidyl-thio, each of which may optionally be mono- or polysubstituted by $C_1$-$C_{12}$-alkyl, $C_1$-$C_{12}$-alkoxy and/or aryl.

3. The process for preparing a rylenetetracarboxylic dianhydride, or a salt thereof having formula Ib as claimed in claim 1, wherein m is 2.

4. The process for preparing a rylenetetracarboxylic dianhydride, or a salt thereof having formula Ib as claimed in claim 1, comprising subjecting a rylenetetracarboximide of general formula II to a hydrolysis under alkaline conditions in the presence of a polar organic solvent and removing the rylenetetracarboxylic dianhydride Ib from any rylenetetracarboxylic monoimide monoanhydride of formula Ia which is formed.

5. The process for preparing a rylenetetracarboxylic dianhydride, or a salt thereof having formula Ib as claimed in claim 1, comprising hydrolyzing the rylenetetracarboximide of general formula II under conditions that form the compound of formula Ib and substantially no rylenetetracarboxylic monoimide monoanhydride of the formula Ia.

6. The process for preparing a rylenetetracarboxylic dianhydride, or a salt thereof having formula Ib as claimed in claim 4, wherein the polar organic solvent is at least one selected from the group consisting of branched and unbranched aliphatic alcohols which have from 3 to 8 carbon atoms.

7. The process for preparing a rylenetetracarboxylic dianhydride, or a salt thereof having formula Ib as claimed in claim 4, comprising subjecting a rylenetetracarboximide of general formula II to a hydrolysis in the presence of a metal fluoride.

8. The process for preparing a rylenetetracarboxylic dianhydride, or a salt thereof having formula Ib as claimed in claim 4, wherein R is phenylthio, pyridyloxy, pyrimidyloxy, pyridylthio or pyrimidyl-thio, each of which may optionally be mono- or polysubstituted by $C_1$-$C_{12}$-alkyl, $C_1$-$C_{12}$-alkoxy and/or aryl.

9. The process for preparing a rylenetetracarboxylic dianhydride, or a salt thereof having formula Ib as claimed in claim 6, wherein R is phenylthio, pyridyloxy, pyrimidyloxy, pyridylthio or pyrimidyl-thio, each of which may optionally be mono- or polysubstituted by $C_1$-$C_{12}$-alkyl, $C_1$-$C_{12}$-alkoxy and/or aryl.

10. The process for preparing a rylenetetracarboxylic dianhydride, or a salt thereof having formula Ib as claimed in claim 7, wherein R is phenylthio, pyridyloxy, pyrimidyloxy, pyridylthio or pyrimidyl-thio, each of which may optionally be mono- or polysubstituted by $C_1$-$C_{12}$-alkyl, $C_1$-$C_{12}$-alkoxy and/or aryl.

11. The process for preparing a rylenetetracarboxylic dianhydride, or a salt thereof having formula Ib as claimed in claim 4, wherein m is 2.

12. The process for preparing a rylenetetracarboxylic dianhydride, or a salt thereof having formula Ib as claimed in claim 8, wherein m is 2.

* * * * *